(12) United States Patent
Neoh et al.

(10) Patent No.: US 11,617,862 B2
(45) Date of Patent: Apr. 4, 2023

(54) CATHETER DEVICES WITH BLOOD CONTROL SYSTEMS AND RELATED METHODS

(71) Applicant: B. Braun Melsungen AG, Melsungen (DE)

(72) Inventors: Kit Weng Neoh, Penang (MY); Boon Ping Neoh, Penang (MY)

(73) Assignee: B. Braun Melsungen AG, Melsungen (DE)

( * ) Notice: Subject to any disclaimer, the term of this patent is extended or adjusted under 35 U.S.C. 154(b) by 293 days.

(21) Appl. No.: 16/625,543

(22) PCT Filed: Jul. 5, 2018

(86) PCT No.: PCT/IB2018/000718
§ 371 (c)(1),
(2) Date: Dec. 20, 2019

(87) PCT Pub. No.: WO2019/008432
PCT Pub. Date: Jan. 10, 2019

(65) Prior Publication Data
US 2022/0001145 A1   Jan. 6, 2022

Related U.S. Application Data

(60) Provisional application No. 62/528,884, filed on Jul. 5, 2017.

(51) Int. Cl.
*A61M 25/00* (2006.01)
*A61M 25/06* (2006.01)
(Continued)

(52) U.S. Cl.
CPC .... *A61M 25/0606* (2013.01); *A61M 25/0097* (2013.01); *A61M 25/0618* (2013.01);
(Continued)

(58) Field of Classification Search
CPC ........ A61M 2039/226; A61M 25/0606; A61M 25/00097; A61M 25/0097; A61M 39/24;
(Continued)

(56) References Cited

U.S. PATENT DOCUMENTS 8,679,063 B2 * 3/2014 Stout ................. A61M 25/0045
604/164.01
2006/0155245 A1 7/2006 Woehr
(Continued)

FOREIGN PATENT DOCUMENTS

CN 104043186 A 9/2014
CN 105407953 A 3/2016
(Continued)

OTHER PUBLICATIONS

What IV needle size should I use?, Nov. 23, 2015, Infusion Nurse Blog, p. 2 (Year: 2015).*
(Continued)

*Primary Examiner* — Bhisma Mehta
*Assistant Examiner* — Phoebe Anne Staton
(74) *Attorney, Agent, or Firm* — KOS IP Law LLP

(57) ABSTRACT

Needle assemblies and related methods having a needle hub with a needle, a catheter tube with a catheter hub and having the needle extending through the catheter tube, a valve positioned in an interior cavity of the catheter hub, a valve opener proximal of the valve, and a needle guard extending at least partially into the valve opener. The valve opener can be used with a range of needle sizes.

20 Claims, 6 Drawing Sheets

(51) Int. Cl.
*A61M 39/24* (2006.01)
*A61M 39/22* (2006.01)

(52) U.S. Cl.
CPC .......... *A61M 39/24* (2013.01); *A61M 25/0693* (2013.01); *A61M 2039/226* (2013.01); *A61M 2039/2426* (2013.01); *A61M 2207/00* (2013.01)

(58) Field of Classification Search
CPC .......... A61M 25/0693; A61M 25/0618; A61M 5/3273; A61M 5/3293; A61M 5/46; A61M 39/0693; A61M 5/1626; A61M 5/3202; A61M 5/321; A61M 25/0612; A61M 25/0631; A61B 2017/3405
See application file for complete search history.

(56) References Cited

U.S. PATENT DOCUMENTS

| | | |
|---|---|---|
| 2012/0271235 A1 | 10/2012 | Fuchs et al. |
| 2012/0277680 A1 | 11/2012 | Woehr et al. |
| 2015/0151085 A1* | 6/2015 | Tan ............... A61M 5/3205 604/164.08 |
| 2016/0158526 A1 | 6/2016 | Woehr |
| 2016/0331937 A1 | 11/2016 | Teoh |
| 2016/0361519 A1* | 12/2016 | Teoh ............... A61M 25/0618 |
| 2018/0214682 A1* | 8/2018 | Woehr ............... A61B 5/15003 |
| 2019/0262586 A1* | 8/2019 | Neoh ............... A61M 25/0693 |

FOREIGN PATENT DOCUMENTS

| | | |
|---|---|---|
| CN | 105939753 A | 9/2016 |
| CN | 106456958 A | 2/2017 |
| EP | 3058977 A1 | 8/2016 |
| JP | 2016538933 A | 12/2016 |
| WO | 2017029374 A1 | 2/2017 |
| WO | WO 2017/029361 A1 | 2/2017 |

OTHER PUBLICATIONS

International Preliminary Report on Patentability (Chapter I) on corresponding PCT application (PCT/IB2018/000718) from International Searching Authority (EPO) dated Jan. 16, 2020.
International Search Report and Written Opinion on corresponding PCT application (PCT/IB2018/000718) from International Searching Authority (EPO) dated Oct. 18, 2018.
Office Action related foreign application (CN Application No. 201880057685.X) from the National Intellectual Property Administration, P.R. China dated Jul. 2, 2021.
International Search Report and Written Opinion on corresponding PCT application (PCT/EP2019/084247) from International Searching Authority (EPO) dated May 12, 2020.
Office Action related foreign application (CN Application No. 201880057685.X) from the National Intellectual Property Administration, P.R. China dated Jan. 18, 2022.
Decision of Rejection related foreign application (CN Application No. 201880057685.X) from the National Intellectual Property Administration, P.R. China dated Jul. 13, 2022.
Office Action related foreign application (EP Application No. 18750474. 1) from the European Patent Office dated Aug. 22, 2022.
Office Action related foreign application (JP Application No. 2020-522798) from the Japan Patent Office dated Jul. 26, 2022.

* cited by examiner

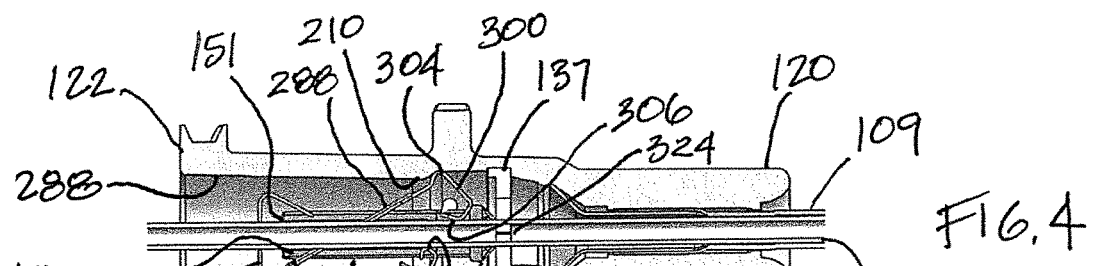

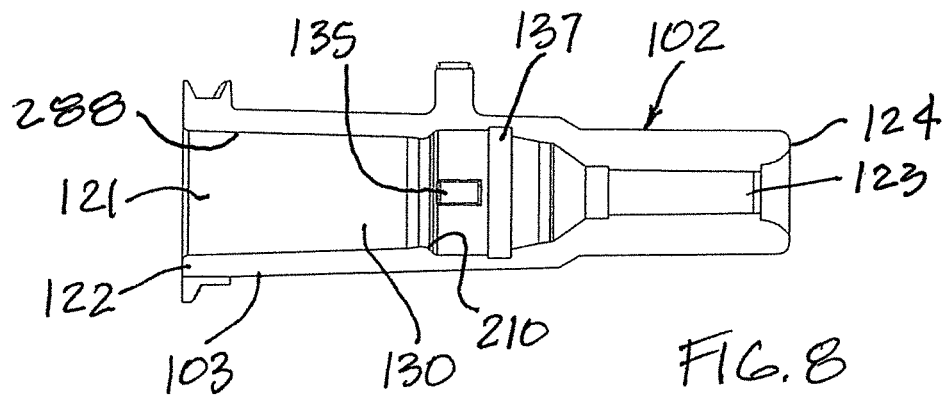
FIG. 8
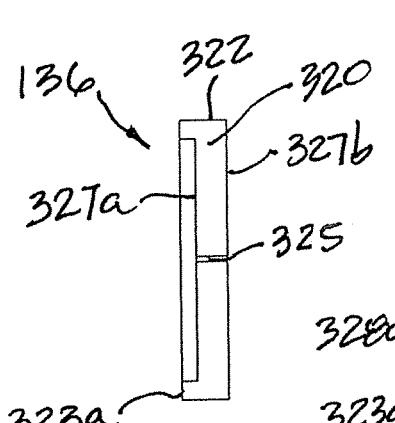
FIG. 9A
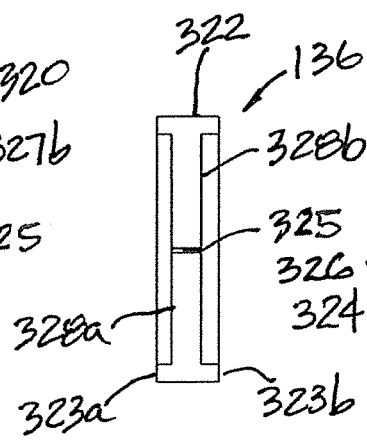
FIG. 9B
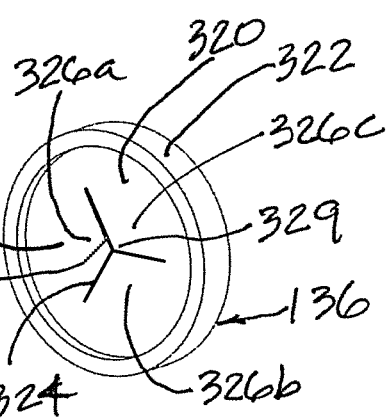
FIG. 9C
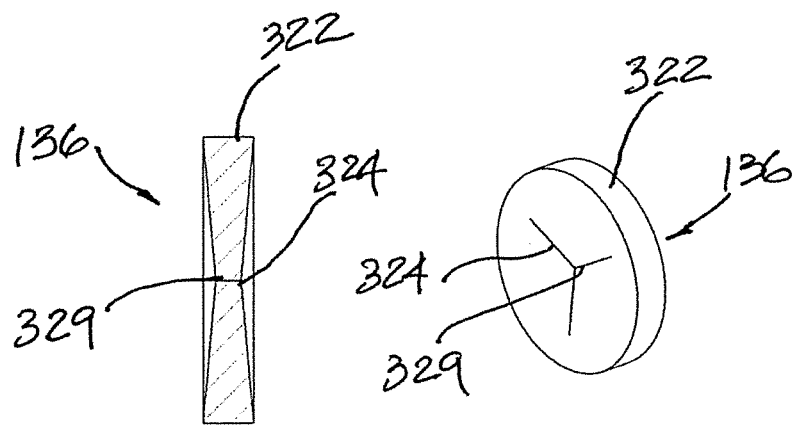
FIG. 10A
FIG. 10B

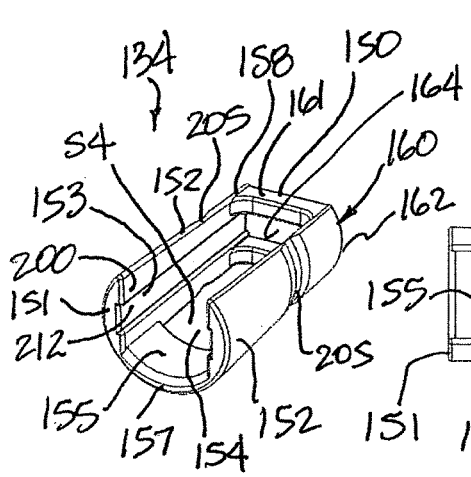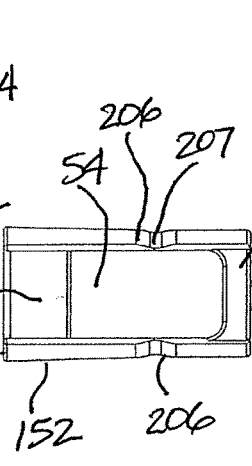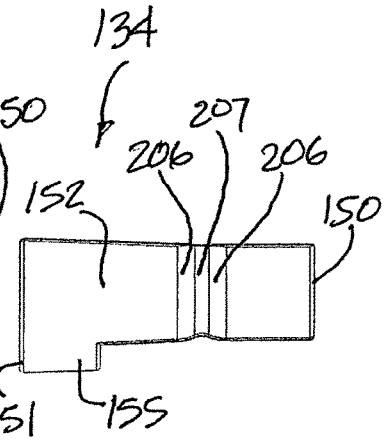
FIG. 11A  FIG. 11B  FIG. 11C
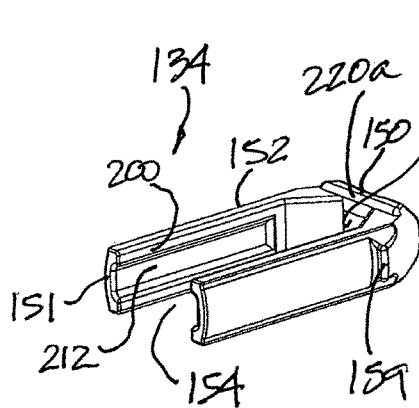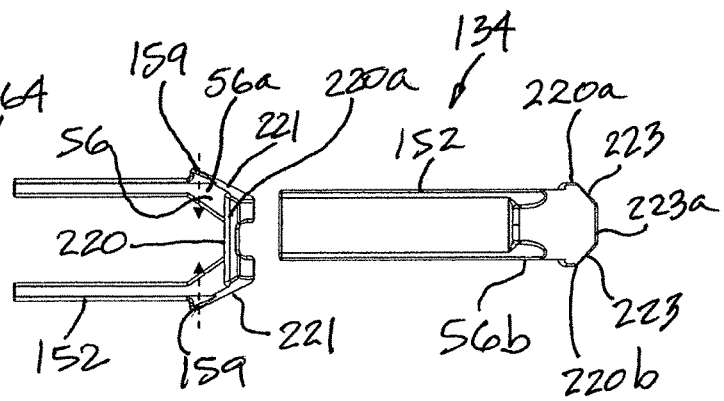
FIG. 12A  FIG. 12B  FIG. 12C

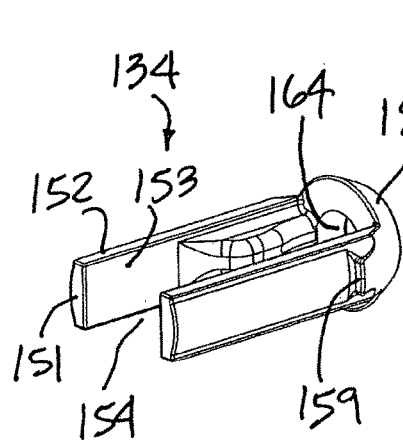
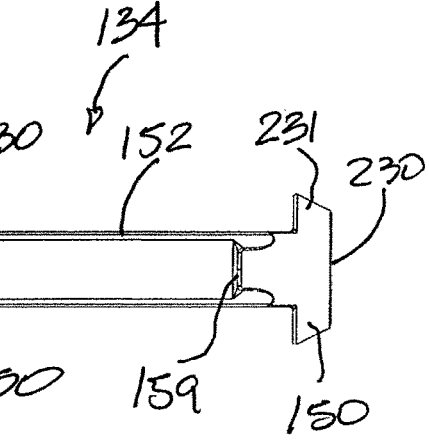
FIG. 13A    FIG. 13B    FIG. 13C
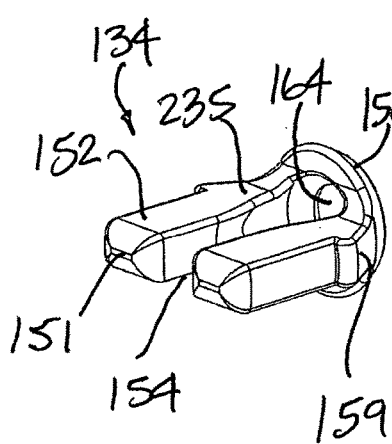
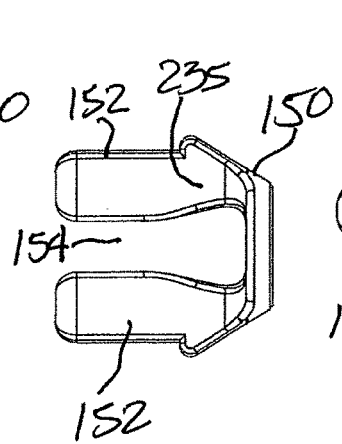
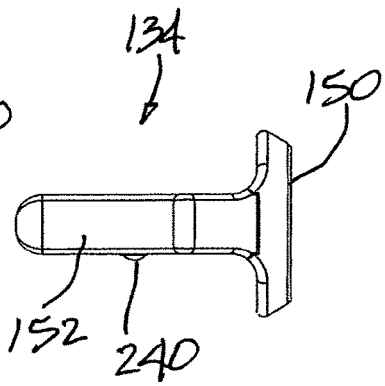
FIG. 14A    FIG. 14B    FIG. 14C

CATHETER DEVICES WITH BLOOD CONTROL SYSTEMS AND RELATED METHODS

FIELD OF ART

The disclosed invention generally relates to needle devices and intravenous (IV) infusion devices, including IV catheters. In particular, IV catheter assemblies having a valve and a valve actuator for opening the valve are disclosed.

BACKGROUND

IV catheters are commonly used for a variety of infusion therapies, including infusing fluids into a patient, withdrawing blood from a patient, or monitoring various parameters of the patient's vascular system. Catheters are typically connected to a catheter adapter that accommodates the attachment of IV tubing to the catheter. Blood control catheters include an internal blood control valve that is opened by the insertion of a male Luer or other object into a proximal end of the catheter adapter. Non-limiting examples of blood control valves are disclosed in United States Patent Application Publication No. 2011/0046570, filed Aug. 20, 2009, titled "Systems and Methods for Providing a Flushable Catheter Assembly." Following placement of the catheter into the vasculature of a patient, an IV fluid source can be connected to the catheter adapter or catheter hub, opening the blood control valve. Thus connected, fluid from the IV source can begin flow into a patient through the catheter.

As is well known in the art, typical blood pressure is 10 to 20 centimeters of water. Infusion bags are usually placed about 100 cm above the patient's heart to direct flow into the patient. At roughly that height, the pressure exerted by the fluid from the infusion bag is much greater than the blood pressure of the patient and therefore can flow into the patient.

Some catheter adapters permit verification of proper placement of the catheter in the blood vessel before fluid infusion begins, such as by providing a flashback chamber of the catheter assembly where a "flashback" of blood can be observed. To confirm flashback in catheter assemblies that do not include a blood control valve, a clinician must manually occlude the vein to prevent undesirable exposure to blood. In contrast, blood control valves can eliminate the need for such manual occlusion, while also reducing the likelihood of blood exposure during catheter placement.

SUMMARY

Needle assemblies are disclosed, which can include over-the-needle catheter assemblies and safety intravenous catheter (IVC) assemblies. Methods of use and of making needle assemblies and their components form part of the present disclosure.

The needle device can have configurations as described in the various embodiments or can be varied by incorporating features from the described embodiments.

An aspect of the present disclosure can include a catheter assembly, which may more broadly be referred to as a needle assembly, a safety needle assembly, or a needle device.

The catheter assembly can have a blood control system implemented therewith.

The catheter assembly can comprise a catheter hub with a catheter tube attached to a hub body of the catheter hub and a needle hub with a needle having a needle shaft extending through the catheter hub and the catheter tube with a needle tip of the needle extending out a distal end or distal opening of the catheter tube in a ready to use position or ready position.

In the ready position, the catheter assembly can be used to perform a venipuncture or intravenous access.

Before use, a protective cap may be required to be removed from the catheter assembly or needle assembly to expose the needle the catheter tube for venipuncture or intravenous access.

A flashback plug can be provided at the proximal end of the needle hub to allow air to vent but can stop blood from spilling out the proximal opening of the needle hub when blood enters the flashback chamber during primary flashback.

Alternatively, a male medical implement such as a syringe can be attached to the proximal end of the needle hub.

The needle hub can further comprise a shoulder, a tab, or a surface feature that physically contacts the catheter hub, such as the proximal end surface of the catheter hub, to axially register the catheter and needle hubs to set the length of the needle tip projecting out of the distal opening of the catheter tube.

In some examples, rather than the needle hub physically contacting the catheter hub, a third hub can be located between the needle hub and the catheter hub and the needle hub contacting the third hub. When used, the third hub can be a housing. The housing of the third hub can accommodate a needle guard, needle device, biasing element, or spring element for shielding the needle tip from inadvertent needle-sticks.

The catheter hub can have a proximal opening and a perimeter defining the proximal opening at a proximal end surface.

The opening at the proximal end of the catheter hub can be sized to receive a male Luer tip. The catheter hub can have external threads and the male Luer tip can have a threaded collar to engage the catheter hub in a Luer lock.

The hub body of the catheter hub can have an interior surface that defines an interior cavity and can have a distal opening at a distal end surface opposite the proximal end surface.

The catheter hub can be a standard catheter hub, a ported catheter hub, or an integrated catheter hub with a tubing extending from a side tubing port.

The catheter hub can include a pair of wings. The pair of wings can incorporate adhesive dressing or medical dressing to facilitate securing the catheter hub to a patient.

A tip protector or needle guard can be provided inside the interior cavity of the catheter hub.

A valve actuator or valve opener can be provided inside the interior cavity of the catheter hub.

A valve for occluding fluid flow can be provided inside the interior cavity of the catheter hub.

A bushing can be provided inside the interior cavity of the catheter hub.

A valve opener can be configured to slide into and push open the valve when advanced by a male Luer tip. The needle shaft of the needle can extend through the needle guard, the valve opener, a valve opening defined by one or more slits of the valve, the bushing, and the catheter tube in a ready to use position.

A valve may be elastically opened so that the needle shaft can pass through the valve opening. The valve can be of the types disclosed in U.S. Pat. No. 9,114,231 to Woehr et al., the contents of which are expressly incorporated hereby reference.

A catheter hub can include a pair of slots of desired depth formed in the interior cavity of the catheter hub to guide axial displacement of a valve opener when the valve opener is actuated, such as when advanced by a syringe tip or a male Luer tip of an IV administration set or an extension set. In an example, the valve opener can have a projection or projections that move within the pair of slots.

The slots can be spaced from one another, such as equally spaced along the inner circumference of the catheter hub or unequally spaced. The slots can each have a rectangular opening and a length of the opening orientated parallel to the lengthwise axis of the catheter hub. In other examples, the slots can have other shaped openings. In other examples, there can be only one slot or more than two slots. The number of slots can depend on structures or features incorporated with the valve opener, which can interact with the slots to align or retain the valve opener within the catheter hub.

A groove may be formed inside the interior cavity of the catheter hub to function as a seat for seating a valve, such as to surround and secure an outer perimeter of the valve inside the catheter hub. The groove can be circumferential or ring shape and can be located distally of the slots.

A guard engagement section can be located proximally of the slots and can be provided to secure the needle guard in the ready to use position and during needle withdrawal prior to activation of the needle guard as further discussed below. The guard engagement section can comprise an internal projection, such as a first inside diameter section located adjacent a second inside diameter section, which can be larger than the first inside diameter section.

The internal projection can be continuous or non-continuous, such as made from several spaced sections. The order or location of the groove, the slots, and the guard engagement section can vary from the sequence described to accommodate different valves, valve openers, and/or needle guards. The proximal end of the catheter hub can be sized with a female Luer taper to receive a male Luer tip. The bushing can be configured to retain the catheter tube to the catheter hub. In one example, the bushing can wedge the proximal end of the catheter tube against the interior wall surfaces of the catheter hub to retain the catheter tube to the catheter hub.

The needle guard may embody any number of prior art guards, tip protectors, or safety clips configured for blocking or covering the needle tip of the needle. In the exemplary embodiment shown, the needle guard can embody one of the guards shown in U.S. Pat. No. 6,616,630, the contents of which are expressly incorporated herein by reference.

In an example, the needle guard can have a proximal wall having a proximally facing wall surface and a distally facing wall surface with a perimeter defining an opening and two resilient arms. The two resilient arms can extend directly or indirectly from the proximal wall.

The needle can comprise a change in profile, which can be an attachment or sleeve, a crimp, or a bulge, for engaging the perimeter on the proximal wall of the needle guard to retract the needle guard in the proximal direction out of the catheter hub following successful venipuncture, as further discussed below.

In the ready to use position, the proximal wall of the needle guard may be in contact with a distal end of the needle hub, such as to a nose section, a tab, or a fin at a distal end of the needle hub. The two arms of the guard can intersect along a side view as described in U.S. Pat. No. 6,616,630, or they can run along different sides of the needle, or different side edges of the proximal wall, and do not intersect along a side view. In one example, one arm can be longer than the other arm.

Each arm of the needle guard can also include different sections of different arm widths, including a first arm section of a first width and a second arm section of a second width, which is smaller than the first width. The two arms can originate from different ends of the proximal wall and can cross one another at their respective second arm sections. Thus, when viewed from a side along the lengthwise direction of the needle guard, the two arms intersect one another. When used with a needle, the two arms intersect one another when in a ready to use position and when in the protective position.

In an alternative embodiment, the two arms originate from different ends of the proximal wall and extend in a distal direction without crossing one another. Thus, the two arms can also have essentially the same arm width along the length of each respective arm.

The needle guard may be folded from a stamped metal sheet to form the guard as shown herein. Ribs may be formed on the arms, the proximal wall, and/or distal walls to increase structurally rigidity. In some examples, the needle guard can be assembled from different components or parts and can include both metal and non-metal parts.

A distal wall can be provided at an end of each arm of the needle guard. The distal walls on the two arms can overlap one another along an axial direction of the needle guard when the arms close over the needle tip by utilizing different arm lengths and/or angling one of the walls at intersections with the resilient arms so that they are positioned serially along the length of the needle. The intersection between a distal wall and the elongated portion of an arm may also be referred to as an elbow or a diagonal diameter of the needle guard when referring to the two elbows on the two arms.

In an example, an intersection or elbow between the distal wall and the resilient arm can engage the guard engagement section inside the catheter hub to secure the needle guard to the catheter hub in the ready to use position, as shown in FIG. 3, and during the process of removing the needle from the catheter hub, as shown in FIG. 4.

The guard engagement section can prevent the needle guard from moving proximally before the needle guard is activated to cover or block the needle tip in the protected position. In some examples, the two distal walls of the needle guard can be called or be considered part of the two arms.

The needle guard arms can be biased outwardly by the needle shaft in the ready position, as shown in FIG. 4, or by a pair of clip seats of the valve opener. When the arms are biased outwardly, the radial profile of the needle guard increases. When the arms are not biased outwardly, the radial profile of the needle guard decreases, compared to when the arms are biased outwardly.

The arms can be biased outwardly so that the intersections of the two arms engage the guard engagement section of the catheter hub to retain the guard within the catheter hub in the ready to use position and during retraction of the needle following successful venipuncture. Said differently, the needle shaft or the clip seats of the valve opener can apply an outward radial force on the lips or end surfaces formed at the free ends of the two distal walls so as to urge the distal walls, and the arms, outwardly to then engage the intersections with the guard engagement section of the catheter hub, or at least maintain the intersections distal of the engagement section.

In some examples, especially when the arms are only biased outwardly by the clip seats of the valve opener and not by the needle shaft, the engagement section can be omitted or the intersections can be situated inside the catheter hub without engaging the engagement section of the catheter hub, as further discussed below. In still other examples, only one intersection of one of the arms is biased outwardly into engagement with the engagement section of the catheter hub.

Lips can be formed at the free ends of the distal walls of the arms and biased outwardly by the needle shaft. The lips can create friction or drag as the needle is withdrawn proximally following successful venipuncture and prior to needle guard activation. The lips formed at the free ends of the distal walls can be rounded or curved to decrease drag on the needle shaft during needle withdrawal. Alternatively, the lips may be straight or not provided with the needle guard. In other examples, the distal walls are biased outwardly by the clip seats and no drag is generated between the needle shaft and the distal walls.

In an example, the needle guard can be positioned inside a valve opener or between two spaced apart structures of the valve opener so that no part of the free ends of the arms, at the ends of the two distal walls, contact or are biased by the valve opener. In other examples, the valve opener can be sized and shaped so as to bias the two free ends of the needle outwardly. When the valve opener biases the arms outwardly, the needle shaft does not have to also bias the two arms outwardly.

The valve opener of the present disclosure can include an actuator head and a pair of valve opener arms. The valve opener arms can be spaced apart and can extend in the proximal direction from the actuator head, which can also be referred to as an actuator head or actuation end for pushing into a valve to open the valve.

The two valve opener arms of a valve opener can be separated from one another by a width, which width can be larger than the diameter of the needle shaft but smaller than the width of the two free ends of the needle guard. Consequently, the two free ends or lips of the needle guard can press against part of the two valve opener arms, which can be called seat clips or arm seats, and be biased outwardly by the two valve opener arms. Thus, when the needle shaft is retracted from the catheter hub following vascular access, there is no drag or friction generated between the two free ends of the needle guard and the needle shaft, such as the exterior of the needle shaft.

During needle withdrawal following successful venipuncture, the change in profile near the needle tip will eventually move proximally against the perimeter defining the opening on the proximal wall of the needle guard. Said differently, following successful venipuncture, the needle and the needle guard can move relative to one another so that the change in profile contacts the proximal wall at the proximal opening of the needle guard. At this moment, additional proximal pulling force by the change in profile on the proximal wall can overcome the engagement between the intersections at the two arms of the needle guard and the guard engagement section of the catheter hub to retract the needle guard proximally out of the catheter hub.

In one example, the additional pulling force of the needle against the proximal wall of the needle guard can cause one or both arms of the needle guard to elastically bend until the intersections can slide through the clearance defined by the guard engagement section of the catheter hub and escape from the engagement. The clearance of the guard engagement section can also be understood as the minimum interior dimension of the catheter hub. That is, the additional pulling force can be applied to cause one or both arms of the needle guard to elastically deflect such that the radial profile of the needle guard at the intersection is reduced to below the minimum diameter of the guard engagement section.

After the lips of both arms separate from the seat clips or arm seats, or from the two spaced apart valve opener arms, the needle guard can be activated to cover the needle tip. In an example, the two distal walls can move to block the needle tip. In some examples, the guard engagement section can be omitted and/or the intersections do not engage the guard engagement section in the ready position and during retraction of the needle following vascular access when free ends are biased outwardly by the valve opener.

The guard engagement section can be formed in the interior cavity of the catheter hub to hold the needle guard in the ready to use position and during needle withdrawal, such as when the arms of the needle guard are biased outwardly by the needle shaft. The guard engagement section can extend radially inwardly into the interior cavity of the catheter hub to form a minimum diameter inside the catheter hub.

The guard engagement section can have an interference overlap with the diagonal diameter of the needle guard, such as the two intersections of the two arms, to ensure the needle guard is secured in place inside the catheter hub in the ready to use position and during retraction of the needle. A tapered or slanted surface at the two intersections can decrease the pulling force required to disengage the needle guard from the guard engagement section of the catheter hub.

The needle guard can be assembled inside the interior cavity of the catheter hub by pushing the proximal wall of the needle guard with the distal end of the needle hub as the needle hub with the needle is inserted into the catheter hub. In the ready to use position, the needle guard can extend at least partially into a gap (FIGS. 11A, 12A) of a valve opener with the proximal section of the needle guard, such as the proximal wall, located outside or proximal of the valve opener.

The proximal wall of the needle guard can be located proximally of the proximal end surfaces of the valve opener. In another example, the proximal wall of the needle guard can be flush or coplanar with the proximal end surfaces of the valve opener. In yet another example, the proximal wall of the needle guard can be located distally of the proximal most surfaces of the valve opener. In embodiments in which the valve opener biases the two arms outwardly, the distal walls of the two arms either do not fit within the gap of the valve opener or the valve opener is provided with seat clips or arm seats to support the two distal walls, as further discussed below.

When the needle tip is pulled into the needle guard following successful venipuncture, the change in profile on the needle can engage a perimeter defining an opening on the proximal wall of the needle guard. At this moment, the arms of the needle guard may simultaneously or soon thereafter, collapse to their protective position to block accidental contact with the needle tip when clear of the needle shaft or the clip seats of the valve opener. The same working can also be achieved by one of the one arm needle guards described in U.S. Pat. No. 6,616,630, which runs along a side of the needle shaft instead of crossing the needle as shown in some of the embodiments of the '630 patent.

After the needle hub and needle are withdrawn from the catheter hub and the needle tip is secured by the needle guard, the valve opening of the valve can reseal upon itself to prevent or limit blood or other fluid from passing through the valve opening. That is, after withdrawal of the needle shaft from the valve opening, the potential elastic energy stored in the valve generated from the needle shaft deflecting the flaps of the valve surrounding the valve opening can be released and the flaps return to a less deflected or closed position to reseal the valve opening.

The catheter hub can be designed such that an engagement distance "A" between the proximal end of the catheter hub and the proximal end surfaces of the valve opener may be less than or equal to the minimum length of engagement of a male medical implement, such as a syringe tip or a male Luer fitting, into the catheter hub. This can ensure that in the event of a connection of a male lock fitting, the male lock fitting would introduce a longitudinal force onto the valve opener and allow a longitudinal displacement of the valve opener towards the proximal end of the valve to open the valve. In one example, the engagement distance is per ISO standard, as presently established or established in the future.

The catheter hub can also be designed such that a minimum depth "B" of the interior cavity of the catheter hub from the proximal end of the catheter hub may be greater than or equal to the minimum length of the male lock fitting to ensure that in the event of a connection of a male lock fitting, the male lock fitting would have sufficient surface contact area with the female Luer taper at the proximal opening of the catheter hub.

A male Luer lock or a syringe tip can be inserted into the interior cavity of the catheter hub through the proximal opening at the proximal end of the catheter hub to displace the valve opener in a distal direction to press against the valve to open the valve. In one example, when a male Luer lock fitting is attached from the proximal end of the catheter hub, the male Luer lock fitting can contact the valve opener arms. As the lock fitting is threaded with the exterior threads at the proximal end of the catheter hub, the male fitting pushes against the proximal end surfaces of the valve opener arms distally until the head of the valve opener pushes the valve open.

When the valve opens, fluid can pass through the valve opening of the valve. When the lock fitting is subsequently removed, the valve can elastically recover back to reseal the valve opening. As the valve reseals itself, the valve can stop or limit flow through the opening while simultaneously push the valve opener proximally back to its ready to use position or its proximal position thereby allowing multiple use of the blood control system.

In an example, the actuator head of the valve opener can have a frusto-conical shape so as to readily deflect the flaps of the valve in the distal direction to open the valve. The valve flaps of the valve may be made sufficiently resilient, such as by making the flaps thicker, so as to return to its closed position after the male Luer tip is removed and an axial load is no longer applied to the valve actuator. In another example, an elastic element, such as a resilient gasket or a spring, may be incorporated to assist with closing the flaps on the valve. The frusto-conical shape of the actuator head can retain a proximally directed force vector of the flap against the conical surface, which can push the actuator back to its starting position until the flaps are closed again and flow is stopped. Various embodiments of the valve opener and various embodiments of the valve, which may be implemented in the blood control system, are further discussed below.

In another example, a valve opener can comprise an actuator head and at least one valve opener arm, such as a leg element or an elongated extension. In an exemplary embodiment, two valve opener arms can extend from the head in the proximal direction and each can have a length measured in a lengthwise direction of the catheter assembly and a width, measured orthogonally to the length. As shown, the two valve opener arms can be spaced apart and extending from opposite points or sections of the head. The two valve opener arms can be sized and shaped for contact by a male Luer to transfer a distally directed force from the male Luer to the head to then push against the valve to open the valve.

A bridge or stabilizer element connected to the two valve opener arms can add rigidity to the two valve opener arms and provide additional surface area for contact with the male Luer. The bridge can extend from an outer edge of one valve opener arm to an adjacent outer edge of the other valve opener arm to connect the two valve opener arms together without impeding fluid flow through the valve opener or interfering with the needle or the needle guard, which can be located between the two valve opener arms in the ready to use position.

The outer surfaces of the two valve opener arms and the bridge can be arc shaped and piecewise continuous to form a semi or partial circular shaped cross section along a width or radial direction of the valve opener. In an example, proximal surfaces of the valve opener arms and a proximal surface of the bridge can be coplanar. In other examples, the proximal surface of the bridge can locate distally of the proximal surfaces of the two valve opener arms.

In some examples, the outer surfaces of the two valve opener arms can also be tapered in the lengthwise direction to match a taper of the interior cavity of the catheter hub. In one example, the two valve opener arms can taper inwardly from the proximal surfaces of the valve opener arms to match the female Luer taper at the proximal end of the catheter hub. The bridge can extend a short distance in the distal direction to provide a through opening or through hole cooperatively defined between the bridge, the two valve opener arms, and the head.

The through opening can be provided to enable an intersection of one of the arms of the needle guard to project therethrough to engage the guard engagement section of the catheter hub. Alternatively or additionally, the intersection can engage the distal edge of the bridge to retain the guard in the ready to use position and during retraction of the needle. In some examples, the bridge can extend to the head and no through opening or through hole is provided between the two valve opener arms and the bridge. The thickness of the bridge can be sufficiently thin such that during assembly, at least one of the arms of the needle guard can elastically deform to move pass the bridge along the longitudinal axis without causing permanent deformation or damage to the needle guard during assembly and during activation of the needle guard.

The thickness of each of two valve opener arms can be sufficiently small or thin so that the needle guard and the two valve opener arms have sufficient clearance to fit within the interior cross-sectional space of the catheter hub without being physically binding against the catheter hub and rendered unmovable or fixed. In an example, the thickness of each of two valve opener arms and the width of the needle guard are such that no undercut or channel is required to be formed in the interior wall surfaces of the catheter hub to accommodate them. When the valve opener arm has an arc cross section, it may be structurally stronger to handle a greater load when being pushed by a male tip to push the head against the valve. This can allow a thin and compact design for the infusion device and gives more room in the standardized space of a female Luer taper.

The valve opener can be made from a metal material or from a polymer material. When made from a metal material, the valve opener can be formed by deep draw methods or punching or cutting a pattern from a sheet metal and bending the stamped or cut pattern to form features of the valve opener including the head and the at least one valve opener arm. Some welding to join individual components are contemplated. The at least one valve opener arm can be bent further to form an arc-shaped cross section to provide added rigidity when pushed by the male Luer. In one example, the valve opener is formed from a stamped stainless steel pattern worked into a desired shape. When made from a polymer material, the valve opener can be molded as a single piece. In some examples, the valve opener can be co-molded or insert molded to form surface features and/or to incorporate different materials. In one example, the polymer material can be a high-strength semi-rigid or rigid material.

Each valve opener arm can comprise at least two lengthwise flanges and a recessed channel defining a drain between the two flanges at an interior surface of each of the two valve opener arms. The two flanges on each arm can have equal widths with unequal widths contemplated. The width of the channel defining the drain can be the same as or different from the width of the flanges. The drains are optional and when incorporated can provide additional flow space for fluid flow along the length of the valve opener, between the two valve opener arms.

A gap between two arms or two elements of a valve opener can provide clearance or space for fluid flow flowing thereacross, such as during IV infusion, and accommodate a needle guard. The structural rigidity of each valve opener arm can remain relatively the same when the drains are incorporated but can increase the fluid flow space beyond the gap.

An undercut can be formed on the exterior circumference of the valve opener and can be located on the exterior of the valve opener arms. The undercut can be sized, shaped, and located on the valve opener so that it seats distal of the guard engagement section or so that the guard engagement section can secure the valve opener within the interior of the catheter hub from displacing proximally out of the catheter hub. The configuration of the undercut, such as the curve, the dimension, the width, the height, etc., can be selected to allow easy axial displacement of the valve opener towards the valve and back and be retained by the guard engagement section.

The undercut on the valve opener can have two sidewalls separated by a bottom surface, similar to a recess or groove. The two sidewalls can be perpendicular to the bottom surface or tapered outwardly to form an opening wider than the width of the bottom surface. The depth of the undercut can allow the valve opener to slide freely. The amount of axial displacement can be limited by the width of the bottom surface or the sidewalls interacting with the guard engagement section. The shape of the undercut and its relative position to the guard engagement section can also cause the actuator head to contact and/or provide a slight axial load against the proximally facing surface of the valve even when the valve opener is not axially loaded or pushed by a male Luer tip.

The actuator head of the valve opener can comprise a body with an outer perimeter. In an example, the outer perimeter can be generally rectangular with two opposing flat surfaces that align with the opening of the gap. The perimeter further comprises two opposing arc-shaped side surfaces, which are continuous with the arc-shaped surfaces of the valve opener arm. In other examples, the outer perimeter can have a taper extending outwardly from a distal end to a proximal end to form a wedge. Interiorly, the body can comprise a through opening formed through the head and in fluid communication with the gap to allow fluid to pass through the valve opener.

The drains of the valve opener arms can extend through the head and form part of the through opening. Thus, fluid can pass through the opening as well as around the head over the flat surfaces. If the bridge extends from the proximal surfaces of the valve opener arms to the head without a through opening, such as a full length bridge, fluid can be forced to pass through the opening and around a single flat surface, on a side opposite the full length bridge.

In an alternative embodiment, the distal side or surface of the actuator head of the valve opener can include a taper or frusto-conical nose section to facilitate opening the valve, such as to deflect the flaps of the valve.

In another example, a valve opener can comprise a head and a pair of valve opener arms, which may also be referred to as leg elements or elongated extensions, extending in a proximal direction, either directly or indirectly, from the head. The valve opener shares similar aspects with the valve opener of FIGS. 11A-11C, except that the head can be shaped differently to generate a different deflection on the valve to open the valve and to aid in retracting the valve opener proximally when the male medical implement is removed, which allows the valve to close.

The valve opener can be without any bridge. Additionally, a pair of guide tabs can extend from opposite sides of the valve opener, such as radially of the two valve opener arms, to restrict movement of the valve opener to an axial direction within a limited range. For example, the guide tabs can cooperate with the slots in the interior cavity of the catheter hub to confine movement of the guide tabs therein and hence movement of the valve opener.

Upon insertion of the valve opener into the catheter hub during installation of the valve opener, the guide tabs can create a sound, such as a click, to provide audible feedback. The shape of the guide tabs and their relative positions to the slots can also cause the actuator head to contact and/or provide a slight axial load against the proximally facing surface of the valve even when the valve opener is not axially loaded or pushed by a male Luer tip.

The two valve opener arms can attach at their respective distal ends to base members of the actuator head. Each base member can have a tapered surface along the interior and a tapered surface on the exterior, relative to the gap located in the interior. As shown, the guide tabs extend from the exterior tapered surfaces. In a particular example, the guide tabs can be located at the proximal ends of the two exterior tapered surfaces.

The head can further comprise a generally flat rectangular frame having two lengthwise edges extending elevation-wise above and below the edges of the two arms and having a through opening for needle access and for fluid flow. Two distally directed projections can extend from the generally flat rectangular frame and having the through opening located therebetween. In some examples, the exterior tapered surfaces can extend continuously to the distal ends of the two distally directed projections to form actuating projections on the head to push open a valve.

In an example, the distal ends of the distally directed projections can have a generally flat or planar surface. In other examples, the distal ends can be rounded or arcuate. The arcuate shaped distally directed projections can maintain a pair of component forces when pushed against the resilient flaps of the valve, which allow the flaps to return to their more relaxed positions when no longer pushed by the valve opener.

Guide tabs can be provided to guide the valve opener within the catheter hub. The guide tabs can each have a width that extends between the edges of the respective valve opener arm. In other examples, the widths of the guide tabs can be substantially the same as the widths of the arms. Optionally, the widths can be smaller. The guide tabs and the head can resemble a U-shape structure with two projections extending axially of the head and having a through opening located therebetween for needle access and fluid flow.

The guide tabs can be configured to slide axially back and forth inside the horizontal slots formed in the interior cavity of the catheter hub when the valve opener is mounted therein. The horizontal slots, having a defined length, can guide the guide tabs of the valve opener and restrict the range of axial displacement.

Each horizontal slot can embody an undercut with a length extending along the axial direction and sized to at least allow the valve opener to slide axially to open the valve and to return proximally with the valve closed. The horizontal slots can each have a width larger than a width of the guide tabs and have a depth greater than the outside dimension measured between the two outermost radial points of the guide tabs to prevent the guide tabs from binding or seizing in the horizontal slots.

The gap can be sized to accommodate the needle guard, which can fit between the valve opener arms. The gap can extend between the valve opener arms and tapers at the base members. The tapered portion of the gap can be determined by the tapered surface along the interior. In some examples, the size of the two base members and angle of the tapered surface along the interior can be selected so that the curved lips at the ends of the two distal walls of a needle guard, or the edges of the distal walls if no curved lips are incorporated, rest on the upper and lower planar surfaces of the base members, which can act to bias the two arms outwardly instead of the needle shaft biasing the two arms outwardly.

Optionally, the two curved lips or the distal walls if no curved lips are incorporated can be located proximally of the two base members so that the needle biases the two arms outwardly.

A drain can be located between the two flanges on each valve opener arm and extends from the proximal surface of the arm to the tapered portion of the gap, similar to the drain discussed elsewhere with reference to FIG. 11A. Optionally, the drain can be omitted from one or both valve opener arms.

A valve opener can comprise a head and a pair of valve opener arms, such as a pair of leg elements or elongated extensions, extending in the proximal direction from the head. The valve opener can be similar to the valve opener described elsewhere herein with a few exceptions. In the present embodiment, the head can have a proximal surface that is generally flat and the structure that extends from the proximal surface can have a frusto-conical shape. Additionally, a clip seat can extend from the interior surface of each valve opening arm. The clip, seat can be configured to support the distal walls or lips at the end of the distal walls of the needle guard so that the arms of the needle guard seat against the clip seat instead of the needle shaft in the ready to use position and during needle withdrawal.

The frusto-conical shaped head can have a flat circular front surface transverse to the needle axis at a distal end of the head and a conical tapered surface extending proximally and outwardly from the flat circular front surface to form a conical wedge. The conical shape of the head can assist the valve opener to push open the valve and retract proximally upon the valve closing.

The clip seat can extend from the interior surface of each valve opening arm into a gap. The height of the clip seat measured from the interior surface of the valve opener arm towards the center of the gap can vary along the valve opener arm so long as the needle can extend between the clip seats. The gap between the two clip seats can be smaller than the width of the two distal walls of a needle guard so that the distal walls, or the lips at the ends of the distal walls, can press against the clip seats and bias outwardly by the clip seats.

Each clip seat can have a wide base that extends further into the gap and an elongated body that extends less into the gap than the base. The two wide bases of the two clip seats therefore can define a narrow portion or minimum portion of the gap located between the two valve opener arms.

In one example, a clip seat is formed between the head and about a midpoint of the length of each valve opener arm. The clip seat can narrow the gap and form a transition region to the circular opening extending through the head. The gap can extend between the valve opener arms at the proximal end and begins to converge at a mouth region located at about the midpoint of the valve opener arm to a throat region before it gradually diverges to the circular opening. Said differently, the gap can extend from the proximal end of the valve opener arms to a transitioning region defined by the clip seats extending from the interior surfaces of the valve opener arms at a distal portion of the valve opener arms. The transitioning region can resemble a nozzle or can resemble other structures. The throat region of the nozzle can support the arms of the needle guard.

The thickness of the clip seat can be the same or larger than the outer diameter of the needle so that the safety clip arms seat on an opposite engaging surfaces of the clip seats. Different size needles can be used so long as the thickness of the clip seat is larger than the outer dimeter of the various needles. This allows a uniform valve opener to be used for different needle sizes, such as for a range of needle diameters, and for the valve opener to bias the arms of the needle guard rather than the needle shaft.

Thus, a same valve opener can be used for different needle sizes or a range of needle diameters, such as for needle sizes from G18 to G24. The range is understood to mean that a particular needle shaft diameter can be an 18 gauge needle and can fall into or within a range of needle diameters, such as a needle range of 18 gauge to a 24 gauge needle. In other examples, the range can be greater, such as 14 gauge to 24 gauge. An additional advantage to harmonizing the same valve opener across several different needle sizes is the predictability of the diagonal diameter of the needle guard when biased outwardly by the clip seats and/or the valve opener arms. This in turn can allow for the same minimum inside diameter of the catheter hub, assuming a clip engagement projection is incorporated for engaging the needle guard. The clip seats can also add structural rigidity to the valve opener arms. Edges of the clip seat may be chamfered, curves, or smoothed to allow easy assembly of the needle guard.

A guide structure can be formed on an exterior of each valve opener arm just proximal of the conical tapered surface. The guide structure can form by extending the conical tapered surface of the head and a sharp transition or indentation to define a shoulder on the exterior of each arm. Said differently, the proximal end of the conical tapered 231 of the head can have an outside diameter of a first dimension and the two valve opener arms can define an outside diameter of a second dimension, which is smaller than the first dimension, to define the two guide structures. The first dimension can be larger than the circumference of the projection in the interior cavity of the catheter hub. The guide structure can be provided between the two different dimensions on each arm. Alternatively, the guide structures can extend outwardly anywhere along a length of the valve opener from opposite sides of the valve opener.

The first dimension at the proximal end of the conical tapered surface of the head can be around 10% to 40% smaller than an outer diameter of the valve to ensure that the head of the valve opener would not pass fully through the slits of the opened valve when a male Luer fitting advances the valve opener. This can allow the valve opener to return or retract proximally upon removal of the male Luer and the valve closing, thus allowing multiple use of the blood control system. Alternatively, the valve opener can be sized and shaped so that the guide structures can pass through the opened valve and be stuck distally of the valve making the valve and valve opener a one-time use blood control device. The guide structures and the head can cooperatively form an arrow like structure with a truncated tip.

Horizontal slots can be provided inside the interior cavity of the catheter hub distal of the guard engagement section to guide the valve opener in the axial direction inside the interior cavity. That is, the guide structures can be configured to slide axially back and forth inside horizontal slots formed in the interior cavity of the catheter hub. The shape of the guide structures and their relative positions to the slots can also cause the actuator head to contact and/or provide a slight axial load against the proximally facing surface of the valve even when the valve opener is not axially loaded or pushed by a male Luer tip.

A valve opener in accordance to further aspects of the present disclosure can comprise a head and a pair of valve opener arms, which can also be a pair of leg elements or elongated extensions, extending from opposite sides of the head. The valve opener of the present embodiment shares many similar aspects as the valve opener discussed elsewhere herein with a few exceptions. In the present embodiment, the thickness of each of the valve opener arms can be the same as the clip seats, which can be greater than or equal to the outer diameter of the needle shaft so that the arms of the needle guard, such as the curved lips or distal walls, seat on the engaging surfaces of the clip seats rather than the needle shaft. Said differently, the valve opening arms can have a thickness greater than or equal to the outer diameter of the needle shaft, with engaging surfaces on opposite sides of the valve opener arms to support the arms of the needle guard in the ready to use position. The valve opener arms can cooperatively define a gap from a proximal end of the valve opener arms to the head. The gap can expand at about the midpoint of the valve opener arm to the circular opening extending through the head.

A ridge can be provided on a surface of the valve opener arm, or two ridges on each arm, to catch the safety distal walls of the needle guard to secure the needle guard in the ready to use position or during needle withdrawal prior to activation of the needle guard. Thus, the one or more ridges can act as a guard engagement section to retain the needle guard to the valve opener, in which case the guard engagement section of the catheter hub may be omitted. Said differently, a guard engagement section can be formed on the clip seat of the valve opener to allow at least one of the arms of the needle guard to engage the valve opener in the ready to use position and during retraction of the needle following successful venipuncture instead of engaging the guard engagement section formed on the interior cavity of the catheter hub.

The ridge may be a protrusion with a rounded or arc shape extending from a surface of one or both valve opener arms. The proximal end surfaces of each valve opening arms may also be rounded. The shape of the guide tabs on the two valve opener arms and guide tabs' relative positions to the slots can also cause the actuator head to contact and/or provide a slight axial load against the proximally facing surface of the valve even when the valve opener is not axially loaded or pushed by a male Luer tip. In an example, the guide tabs, the two valve opener arms, and the two clip seats can be formed continuously with a same width. In other examples, the guide tabs can have a different width than the valve opener arms and the clip seats.

Although valve openers can be formed or made by plastic injection molding, valve openers described herein can also be made from a metal material. The valve opener made from a metal material can comprise a head and a pair of valve opener arms, such as a pair of leg elements or elongated extensions, extending from opposite sides of the head. The valve opener of the present disclosure can be formed from a stamped sheet metal and then bent to form features of the valve opener including the head and a pair of valve opener arms extending proximally from opposite sides of the head.

Fingers can extend distally from a center portion of the head that together can define a distal projection having a through passage therebetween. The fingers can form by slitting the surface of the head and then bending the tabs to create fingers that define the distal projection. In an example, there can be four fingers that can form a generally square or rectangular projection. The fingers can act as an opening member to push open the valve when the valve opener is pressed distally into the valve by a male Luer fitting. The shape and number of fingers can vary.

Side wings can extend outwardly and transversely from outside surfaces of the valve opener arms. The side wings can extend transversely from the valve opener arms to form an angle greater between zero degrees and 90 degrees to allow the valve opener to snap-fit into the horizontal slots of the catheter hub. Thus, the side wings are similar to the guide structures on other valve openers described elsewhere and can extend outwardly anywhere along a length of the valve opener of the present embodiment from opposite sides of the valve opener.

A proximal flange can extend outwardly along the transverse axis from the proximal end surface of each valve opener arm to provide additional surface areas for the male Luer conical fitting to press against to push the valve opener in the distal direction to open the valve. Arm flanges can extend outwardly and transversely on opposite lengthwise edges of the valve opener arms to increase the structural rigidity of the valve opener arms. In some examples, the surface of the opener arms can be worked to for a curved shape, such as an arc shape, to increase the strength of the arms against axial load by the male Luer tip.

A valve may be usable with the catheter assemblies and hubs with a female Luer described elsewhere herein. The valve can be called or considered a disc valve. The disc valve can optionally include one or more flanges extending therefrom, as further discussed below. The valve can have a valve body having a width measured from one edge to another edge of an outer perimeter or outer diameter of the valve body. The valve body can have a thickness, which is the dimension that extends orthogonal to the width from a first surface to a second surface. The valve can be seated in a valve seat area or valve groove provided in the interior cavity of the catheter hub. The valve can be configured to be located distal a valve opener to form a seal in the interior cavity and to be opened by the valve opener.

The valve groove can be a radial undercut formed in the interior cavity of the catheter hub with a depth in the range between about 0 mm to about 1 mm deep, or recessed, to allow proper seating. The depth range can have a tighter tolerance of about 0 mm to about 0.3 mm. A seal can be provided between the interior of the catheter hub and the outer surfaces of the valve such as the outer perimeter.

In one example, a slight compressive force can be applied by the catheter hub against the perimeter of the valve to ensure sealing. Alternatively or in addition, the outer edges of the first and second surfaces of the valve body can seal against the surfaces of the valve groove to provide a seal with the catheter hub. In an example, the profile of the valve groove as well as any profile internally of the catheter hub, such as slots or projection(s), can be contoured with radiuses to minimize smearing of material during the molding process of the catheter hub.

A valve opening can extend through the thickness of the valve body from the first surface to the opposite second surface. The thickness of the valve body can be uniform or can vary. The thinner the valve, the less resistance the valve is to opening, and therefore less force required to open the valve. The thicker the valve, the more elastic energy is able to be stored to enable the valve to return to its original pre-opened shape upon elastic deformation, and thus allowing multiple access of the valve opening and closing. In one example, the thickness of the valve is in the range of about 0.3 mm to about 1.5 mm. However, the thickness can vary and can include other ranges.

A first flange can extend axially from the outer perimeter or outer diameter of the valve body to allow better seating of the valve in the catheter hub. The first flange can be oriented in the catheter hub to extend proximally or distally. The first flange and the valve body can cooperatively define a first circular cavity concentric with the valve body and locally reducing the thickness of the valve at the first circular cavity.

The valve opening can include or comprise three slits extending radially from a center of the valve and formed approximately degrees apart, thereby forming a first flap, a second flap, and a third flap. That is, the three slits can intersect at a single central point coinciding with the axis of the valve. In other examples, the slits can be unequally spaced apart. The length of the slits can vary. In one example, the slits extend to the first flange. The first flap, the second flap, and the third flap can be deflected to open a flow path through the valve body. The fluid flow path can be provided when the three flaps are deflected by the valve opener. In an example, the flaps near the central point can expand radially towards the perimeter and in the distal direction when deflected by the valve opener. That is, the first flap, the second flap, and the third flap can be deflected by pushing the valve with one of the valve openers described herein on a proximal side of the valve.

Alternatively, the valve opening can be a single slit formed through the thickness of the valve body and defining a first flap and a second flap, which can also be deflected to open a flow path through the valve body by pushing the valve with a valve opener on one side of the valve.

In an example, the valve opening may also include reliefs embodying two short through cuts at each end of the slit forming a V-shaped relief. The reliefs can provide clearance for the flaps to enable them to deflect more readily when pushed open by the valve opener. Less preferably, a single short through cut may be incorporated at each end of the slit.

A second flange can extend axially from the outer perimeter of the valve opposite the first flange thereby cooperatively forming a second circular cavity concentric with the valve body and further reducing the thickness of the valve at the first and second circular cavities. An alternative valve similar to other valves described elsewhere herein can comprise a circular valve body with a varying thickness that increases from a central point of the valve towards the outer perimeter of the valve. The thickness can vary linearly with a constant slope or can have a complex slope. The valve can have an opening with three slits provided through the thickness of the valve body to form three flaps. The three slits can intersect at a single central point coinciding with the axis of the valve. The flaps can be deflected to open a flow path through the valve body. The first, second and third flaps can be deflected by pushing the valve with a valve opener to deflect the flaps radially and axially. A fluid flow path can be provided when the three flaps are deflected. In an example, the flaps near the central point can expand radially towards the outer perimeter and in the distal direction when deflected by the valve opener pressing against the proximally facing surface of the valve.

The valve can be located inside the catheter hub just distal of the head of the valve opener. The valve can comprise an outer perimeter that can be seated in a valve groove to fix the outer perimeter of the valve between the valve opener and the bushing. Alternatively, the outer perimeter of the valve can be fixed to the interior cavity of the catheter hub between the valve opener and the bushing by interference fit, adhesive, or other securing means.

To remove the needle from the catheter hub with the needle guard covering the needle tip in a protective position, the needle device starts at the position of FIG. 3, which may first require removal of a disposable protective cap, moves to a transition position of FIG. 4 wherein the needle slides proximally relative to the catheter tube and the catheter hub, and then continuing to move the needle until the needle tip moves proximally of two distal walls, one on each end of the resilient arms of the needle guard. The distal walls can be considered part of the arms on the needle guard and are specifically called out so as to identify the structure and function in relations to the other components and how the disclosed needle assemblies operate.

Where the needle guard has only one distal wall and/or one arm, the process is similar but the needle tip only has to move proximally of the one distal wall to cause the needle guard to activate. As the two distal walls and hence the two resilient arms are no longer biased outwardly by the needle or valve opener, the two arms move radially to decrease the guard's radial profile and to disengage from the guard engagement section of the catheter hub. Alternatively, the one arm and one distal wall can disengage from the one guard engagement section.

Where the arms of the needle guard are biased outwardly by the clip seats of the valve opener, the arms remained biased until the change in profile on the needle moves proximally and contacts the perimeter on the proximal wall of the needle guard. Further movement of the needle from that point moves the proximal wall, and hence the entire needle guard, in the proximal direction until the distal walls separate from the clip seats on the valve opener, or from the valve opener arms. At such time, the distal walls move radially inwardly to block the distal tip of the needle in a protective position.

As the needle continues to move in the proximal direction and the change in profile engages the perimeter on the proximal wall of the needle guard, the needle guard is moved proximally with the needle. Alternatively the needle guard can clamp onto the needle shaft and be removed from the catheter hub as a unit without utilizing a needle crimp. Note that in the protective position in which the needle guard covers the needle tip, the valve and the valve opener remain inside the interior cavity of the catheter hub. Thus, the valve and the valve opener can locate inside the catheter hub in both the ready position of the needle and the protective position of the needle. Viewed from another perspective, the valve and the valve opener can be located inside the catheter hub in both the ready to use position of the catheter assembly, in which the needle tip projects out a distal opening of the catheter tube, and a protective position of the catheter assembly, in which the needle is removed from the catheter hub and the needle tip is covered by a needle guard.

A male medical implement or instrument can be a male Luer, a syringe tip, an IV set connector, or other male tip having a Luer taper. The male medical implement can be located in the proximal opening of a catheter hub. For example, the male medical implement can be connected to an IV tubing, which is connected to an IV fluid source for fluid delivery through the male medical implement, the catheter hub, and the catheter tubing to deliver fluid therapy to a patient.

When initially inserting the male medical implement, such as a male tip, into the proximal opening of the catheter hub, the male tip can initially contact the two valve opener arms on the valve opener to advance a distally directed force on the two valve opener arms to open the valve. The proximal end surfaces of the valve opener arms can provide a contact surface for the distal end of the male medical instrument, as previously discussed.

The valve opener arms can also be designed to contact the inside wall of the catheter hub at a tangential point. In this way, the valve opener arms can be stable and can resist being deflected outwards. This arrangement can avoid relatively thin valve opener arms from wedging between the male medical instrument and the inside wall of the catheter hub. The distally directed force moves the valve opener in the distal direction until the geometries of the male tip and the proximal opening of the catheter hub stop further distal advancement of the male tip. In an example, a female Luer taper of the catheter hub and a male Luer taper of the male tip can register to form a Luer engagement and block distal advancement of the male tip further into the opening of the catheter hub. A seal can be provided by the Luer engagement to prevent fluid from leaking out the proximal opening of the catheter hub.

As the valve opener moves distally by the distal advancement of the male tip, the head of the valve opener is urged distally and pushes against the proximally facing surface of the valve. In particular, the distal end of the valve opener initially pushes against the proximally facing surface of the valve. As the valve is fixed inside the catheter hub, the flaps of the valve are urged distally by the valve opener, which is urged distally by the male tip. For example, the head can contact and push the valve in the distal direction thereby opening a flow path through the valve opening of the valve. Fluid from the male tip can then flow through the catheter hub, through the valve, and through the lumen of the catheter tube. Alternatively, a suction can be applied by the male medical instrument, such as a syringe or vacuum blood collection tube, and blood aspirated from the patient. This is often done for testing samples before infusion therapy is commenced. Also, typically any remaining blood is first flushed from the inside of the catheter hub before infusion therapy is commenced.

The shape of the head of the valve opener or features on the head of the various valve openers can facilitate deflection of the flaps on the valve radially outwardly and in the distal direction, and can facilitate retracting the valve opener in the proximal direction to close or seal the valve. The heads can be designed as a one-time use. That is, the heads of the various valve openers can be designed such that they stick to the valve or contact the valve in such a way that does not allow the flaps to uncoil even after removal of the male Luer tip and the no axial load is applied on the valve opener.

Thus, an aspect of the present disclosure is understood to include a catheter assembly comprising a valve comprising comprises plurality of slits defining a plurality of flaps that move in a distal direction to open a flow path through the valve, a valve opener configured to move the flaps of the valve, and a needle guard extending into the valve opener and having distal walls biased radially by the needle shaft or by the valve opener. The biased distal walls of the needle guard can engage a guard engagement section extending from inside the interior cavity of the catheter hub, can engage bumps or projections on the valve opener arms, or not engage any projection or bumps when the distal walls are biased outwardly by clip seats on the valve opener.

To change the male tip or to simply close the valve from the open position, the male tip can be removed in the proximal direction away from the catheter hub, which removes the axial load on the valve opener. The biasing or resilient nature of the valve, which can be made from an elastomer, allows the valve to recoil to its more relaxed state. Thus, the flaps on the valve will recoil by moving proximally, which pushes the valve opener in the proximal direction inside the interior cavity of the catheter hub. The valve opener therefore can return to its original position after removal of the male tip from the catheter hub. In some examples, an elastic gasket or a helical spring may be used in the interior distal chamber of the catheter hub, distal of the valve, to help push the flaps close upon removal of the male Luer tip.

Methods of making and of using the catheter assemblies and their components described elsewhere herein are within the scope of the present disclosure.

A further aspect of the present disclosure can include a needle assembly that can comprise: a needle hub with a needle having a needle shaft and a needle tip extending from a distal end of the needle hub; a catheter hub having an interior surface defining an interior cavity; a catheter tube attached to the catheter hub and having the needle extending through the catheter tube with the needle tip extending out a distal opening in a ready to use position; a valve comprising a plurality of slits and a plurality of flaps defining an opening seated in the interior cavity of the catheter hub; a needle guard comprising at least one arm extending from a proximal wall having a perimeter defining a proximal opening; a valve opener positioned in the interior cavity of the catheter hub and proximal of the valve in a first position, the valve opener comprising a head located distally of the needle guard and two valve opener arms extending in a proximal direction of the head and located in between the needle guard and the interior surface of the catheter hub, each of said two valve opener arms comprising a clip seat having the needle guard biased there against and having a width measured orthogonally to the needle shaft, and wherein the width of the clip seat is larger than a diameter of the needle shaft and larger than a range of diameters of needle shafts; and wherein the head of the valve opener is axially displaceable against the valve to open the valve in a second position.

The range of diameters of needle shafts can be from G18 to G24. In other examples, the range can be different. For example, the range of diameters of needle shafts can be from G14 to G24.

The needle guard can engage a guard engagement section formed on the interior surface of the catheter hub in a ready to use position and during needle withdrawal prior to activation of the needle guard.

The guard engagement section can have an inside diameter and wherein the inside diameter can be generally constant whether used with any number having a needle diameter from G18 to G24.

The valve opener can comprise a pair of guide tabs, one each on an exterior of each respective valve opener arm.

The guide tabs can be located in corresponding slots formed in the interior cavity of the catheter hub.

The guide tabs can produce a sound when engaging the slots. The sound can be a click. The click can emanate from one guide tab or from both guide tabs.

A channel defining a drain can be provided on each of the two valve opener arms.

A bridge can connect two valve opener arms together. The bridge can have an arc shape and the arc shape can contact the interior surface of the catheter hub or be spaced from the interior surface. The bridge can add strength to the two valve opener arms to prevent excessive deflection or buckling.

The head of the valve opener can comprise a frusto-conical shaped distal end.

The guide tabs, the two valve opener arms, and the two clip seats can be formed continuously with a same width.

Yet another aspect of the present disclosure can include a method of making a needle assembly. The method of making can comprise: providing a needle hub with a needle having a needle shaft and a needle tip extending from a distal end of the needle hub; providing a catheter hub having an interior surface defining an interior cavity; attaching a catheter tube to the catheter hub and disposing the needle through the catheter tube with the needle tip extending out a distal opening in a ready to use position; placing a valve comprising a plurality of slits and a plurality of flaps defining an opening in the interior cavity of the catheter hub; placing a valve opener in the interior cavity of the catheter hub proximal of the valve; and placing a needle guard comprising at least one arm extending from a proximal wall having a perimeter defining a proximal opening in contact with the valve opener; wherein the valve opener comprises a head located distally of the needle guard and two valve opener arms extending in a proximal direction of the head and located in between the needle guard and the interior surface of the catheter hub, each of said two valve opener arms comprising a clip seat having the needle guard biased there against and having a width measured orthogonally to the needle shaft, and wherein the width of the clip seat is larger than a diameter of the needle shaft and larger than a range of diameters of needle shafts; and wherein the head of the valve opener is axially displaceable against the valve to open the valve in a second position.

The method can be used a needle shaft having a diameter of a G18 needle.

Using a catheter hub with the same inside minimum diameter and the same valve opener, the method can be used a needle having a diameter of a G20, G22, or G24 needle.

The method wherein the needle assembly is a first needle assembly and the method can comprise making a second needle assembly identical to the first needle assembly and wherein the needle shaft of the second needle assembly has a diameter of a G20 needle, G22 needle, or G24 needle.

Aspects of the present disclosure can include a needle assembly comprising a needle hub with a needle extending from a distal end of the needle hub, a catheter hub having an interior cavity, a catheter tube attached to the catheter hub and having the needle extending through the catheter tube in a ready to use position, a valve seated in the interior cavity of the catheter hub, a needle guard comprising at least one arm extending from a proximal wall, and a valve opener positioned in the interior cavity of the catheter hub and proximal of the valve in a first position, the valve opener comprising a head distal the needle guard, and one or more valve opener arms extending in a proximal direction of the head between the needle guard and the interior cavity of the catheter hub, and wherein the head of the valve opener can be movable through an opening of the valve in a second position.

The needle guard can engage a guard engagement section in a ready to use position and during needle withdrawal prior to activation of the needle guard.

The guard engagement section can extend from the interior cavity of the catheter hub.

The at least one arm can engage the needle shaft in the ready to use position and during needle withdrawal prior to activation of the needle guard.

The at least one arm can engage the one or more valve opener arms of the valve opener in the ready to use position and during needle withdrawal prior to activation of the needle guard. The guard engagement section can extend from the one or more valve opener arms.

The one or more valve opener arms can be a pair of valve opener arms at opposite sides of the valve opener.

A clip seat can extend from an interior surface of each valve opener arm to support the at least one arm of the needle guard.

The one or more valve opener arms can be a pair of valve opener arms at opposite sides of the valve opener.

The valve opener can further comprise a shoulder formed between the head and each valve opener arm.

The shoulders can be received in horizontal slots defined in opposite sides of the interior cavity of the catheter hub. The horizontal slots can limit the range of axial movement of the valve opener.

The valve opener can be biased proximally from the second position to the first position by the valve.

Another aspect of the present disclosure can include a catheter assembly comprising a catheter hub having a proximal opening extending distally into an interior cavity, a catheter tube attached to a distal end of the catheter hub, a valve seated in the interior cavity of the catheter hub, a valve opener positioned proximal of the valve in the interior cavity of the catheter hub, the valve opener comprising a head and a pair of valve opener arms extending proximally of the head, a needle guard extending into a gap between the valve opener arms and comprising at least one arm extending from a proximal wall, the needle guard, and wherein the valve opener is extendable through an opening of the valve.

A guard engagement section can extend from the interior cavity of the catheter hub to secure the needle guard in a ready to use position.

The guard engagement section can form a minimum diameter of the interior cavity of the catheter hub.

The needle guard can bias against the needle shaft in the ready to use position and during needle withdrawal.

A guard engagement section can extend from the pair of valve opener arms to secure the needle guard in a ready to use position.

The needle guard can bias against the pair of valve opener arms in a ready to use position.

The needle guard can bias against a pair of clip seats extending from an interior surface of each of the pair of valve opener arms into the gap.

A shoulder can be formed between the head and each of the pair of valve opener arms.

The shoulders can be received in horizontal slots defined in opposite sides of the interior cavity of the catheter hub. The horizontal slots can limit the range of axial movement of the valve opener.

The head of the valve opener can be tapered.

Methods of making and of using the catheter assemblies and their components described elsewhere herein are within the scope of the present disclosure.

BRIEF DESCRIPTION OF THE DRAWINGS

These and other features and advantages of the present devices, systems, and methods will become appreciated as the same become better understood with reference to the specification, claims and appended drawings wherein:

FIG. 4 is a schematic partial cross-sectional side view of the catheter assembly of FIG. 1 in a transition position or state in which the needle is in the process of being removed from the catheter tube and the catheter hub, such as following successful venipuncture;

FIG. 5 is a partial isometric view of a catheter assembly in the transition position or state in which a needle guard is coupled to a valve opener, and shown without a catheter hub;

FIG. 6 is a schematic cross-sectional side view of the catheter assembly of FIG. 1 in which the needle has completely separated from the catheter hub and the valve opener is available for advancing against the valve to open the valve;

FIG. 7 is a schematic cross-sectional side view of the catheter assembly of FIG. 1 in which the catheter hub is now connected with a male Luer and the valve actuator is advanced by the male Luer to open the valve;

FIG. 8 is a schematic cross-sectional side view of a catheter hub in accordance with aspects of the present disclosure;

FIG. 9A is a schematic cross-sectional side view of a valve embodiment with an extended flange in accordance with aspects of the present disclosure;

FIG. 9B is a schematic cross-sectional side view of another embodiment of a valve with an extended flange on opposite sides of the valve disc in accordance with aspects of the present disclosure;

FIG. 9C is an isometric view of a valve, which can be the valve of FIG. 9A or 9B;

FIG. 10A is a schematic cross-sectional side view of another embodiment of a valve in accordance with aspects of the present disclosure;

FIG. 10B is an isometric view of the valve of FIG. 10A;

FIGS. 11A-C show an isometric view, a top view, and a profile view, respectively, of a valve actuator in accordance with aspects of the present disclosure;

FIGS. 12A-C show an isometric view, a top view, and a profile view, respectively, of a another embodiment of a valve actuator in accordance with aspects of the present disclosure;

FIGS. 13A-C show an isometric view, a top view, and a profile view, respectively, of yet another embodiment of a valve actuator in accordance with aspects of the present disclosure;

FIGS. 14A-C show an isometric view, a top view, and a profile view, respectively, of yet another embodiment of a valve actuator in accordance with aspects of the present disclosure.

DETAILED DESCRIPTION

The detailed description set forth below in connection with the appended drawings is intended as a description of the presently preferred embodiments of catheter assemblies with control valves provided in accordance with aspects of the present devices, systems, and methods and is not intended to represent the only forms in which the present devices, systems, and methods may be constructed or utilized. The description sets forth the features and the steps for constructing and using the embodiments of the present devices, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

Figure 1:
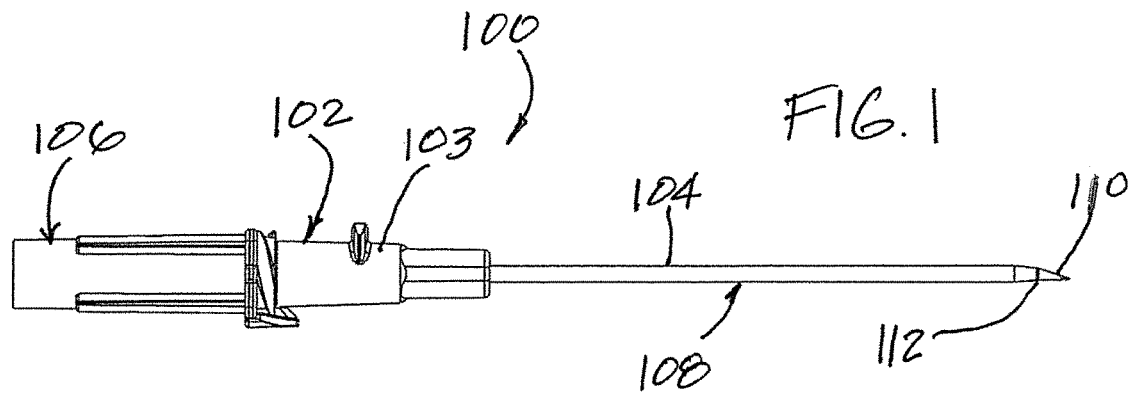
FIG. 1 is a side view of a catheter assembly in a ready position in which the needle tip extends out a distal end of a catheter tube.

With reference now to FIG. 1, a catheter assembly 100, which may more broadly be referred to as a needle assembly, a safety needle assembly, or a needle device, having a blood control system implemented therewith is shown, which comprises a catheter hub 102 with a catheter tube 104 attached to a hub body 103 and a needle hub 106 with a needle 108 having a needle shaft 109 (FIG. 2) extending through the catheter hub 102 and the catheter tube 104 with a needle tip 110 extending out a distal end or distal opening 112 of the catheter tube 104 in a ready to use position or ready position. In the ready position, the catheter assembly 100 is ready for use, such as to perform a venipuncture or intravenous access. Sometimes the ready position first requires removing a protective cap (not shown) from the catheter assembly or needle assembly 100.

Figure 2:
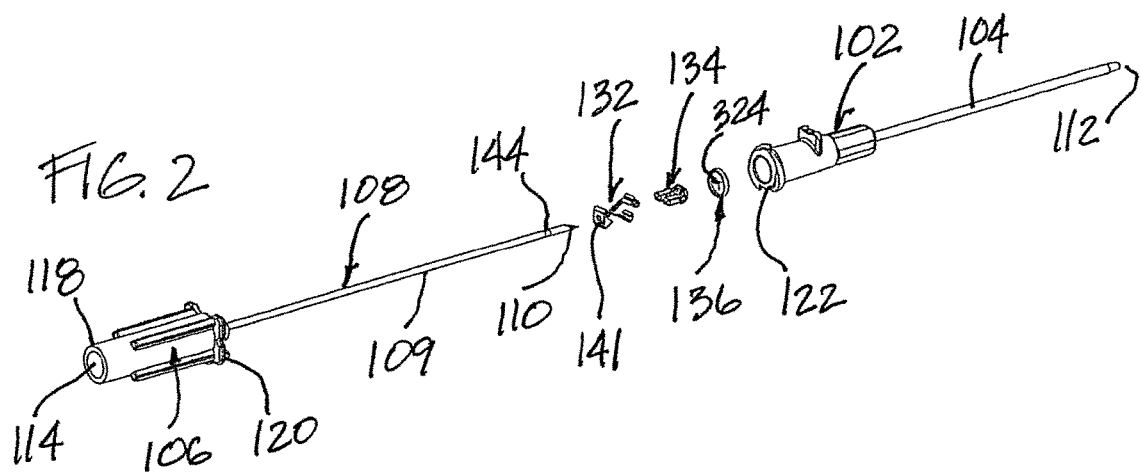
FIG. 2 is an exploded isometric view of the catheter assembly of FIG. 1.
Figure 3:
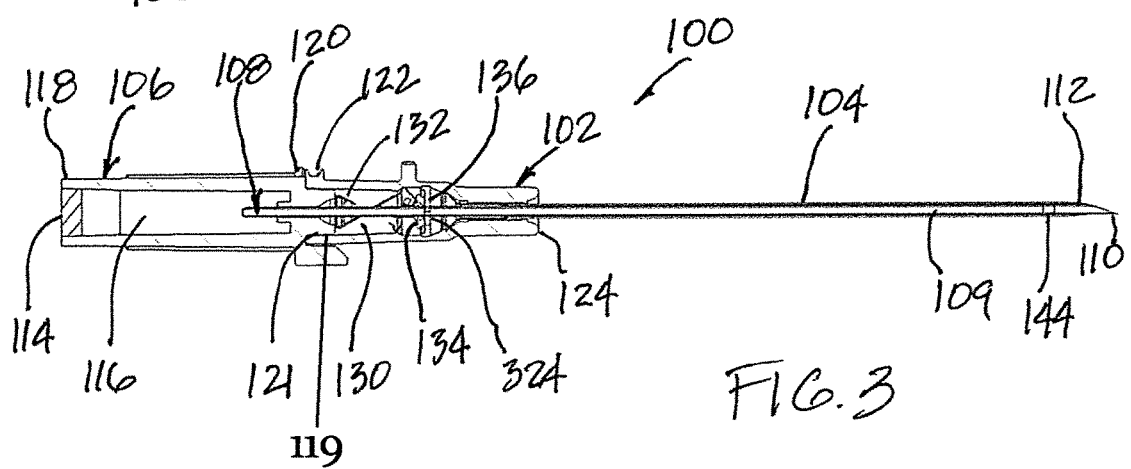
FIG. 3 is a schematic cross-sectional side view of the catheter assembly of FIG. 1.

FIGS. 2 and 3 show an exploded view and a schematic cross-sectional view, respectively, of the catheter assembly 100 of FIG. 1. A flashback plug 114 can be provided at the proximal end 118 of the needle hub 106 to allow air to vent but stops blood from spilling out the proximal opening of the needle hub when blood enters the flashback chamber 116 during primary flashback. Alternatively, a male medical implement such as a syringe can be attached to the proximal end 118 of the needle hub 106.

The needle hub 106 can further comprise a shoulder, a tab, or a surface feature 120 that physically contacts the catheter hub 102, such as the proximal end surface 122 of the catheter hub 102, to axially register the catheter and needle hubs 102, 106 to set the length of the needle tip 110 projecting out of the distal opening 112 of the catheter tube 104.

Jumping ahead to FIG. 8, a schematic cross-sectional side view of the catheter hub 102 of FIG. 1 is shown without the catheter tube. The catheter hub 102 can have a proximal opening 121 and a perimeter defining the proximal opening at a proximal end surface 122. The hub body 103 has an interior surface that defines an interior cavity 130 and has a distal opening 123 at a distal end surface 124 opposite the proximal end surface 122. The catheter hub 102 can be a standard catheter hub, can include a pair of wings, can be a ported catheter hub, or can be an integrated catheter hub with a tubing extending from a side tubing port.

With further reference to FIG. 2 and continued reference to FIG. 8, a tip protector or needle guard 132, a valve actuator or valve opener 134, a valve 136 for occluding fluid flow, and a bushing 138 can be provided inside the interior cavity 130 of the catheter hub 102, as shown in FIG. 4. As further discussed below, the valve opener 134 is configured to slide into and push open the valve 136 when advanced by a male Luer tip. The needle shaft 109 of the needle 108 can extend through the needle guard 132, the valve opener 134, a valve opening 324 defined by one or more slits of the valve 136, the bushing 138, and the catheter tube 104 in the ready to use position. The valve 136 may be elastically opened so that the needle shaft 109 can pass through the valve opening 324, as further discussed below in reference to FIGS. 9A-9C and FIGS. 10A and 10B.

Referring again to FIG. 8, the catheter hub 102 can include a pair of slots 135 of desired depth formed in the interior cavity 130 to guide the axial displacement of a valve opener 134 when the valve opener is actuated, such as when advanced by a syringe tip or a male Luer tip of an IV administration set or an extension set. The slots 135 can be spaced from one another, such as equally spaced along the inner circumference of the catheter hub 102. The slots 135 can each have a rectangular opening and a length of the opening orientated parallel to the lengthwise axis of the catheter hub. In other examples, the slots can have other shaped openings. In other examples, there can be only one slot 135 or more than two slots 135. The number of slots can depend on structures or features incorporated with the valve opener 134, which can interact with the slots to align or retain the valve opener within the catheter hub.

A groove 137 may be formed inside the interior cavity 130 of the catheter hub to function as a valve seat, such as to surround and secure an outer perimeter of the valve 136 inside the catheter hub. The groove 137 can be circumferential or ring shape and can be located distally of the slots 135. A guard engagement section 210 can be located proximally of the slots 135 and can be provided to secure the needle guard 132 in the ready to use position and during needle withdrawal prior to activation of the needle guard 132 as further discussed below. The guard engagement section 210 can comprise an internal projection, such as a first inside diameter section located adjacent a second inside diameter section, which is larger than the first inside diameter section. The internal projection can be continuous or non-continuous, such as made from several spaced sections. The order or location of the groove 137, the slots 135, and the guard engagement section 210 can vary to accommodate different valves, valve openers, and needle guards. The proximal end of the catheter hub 102 can be sized with a female Luer taper to receive a male Luer tip. The bushing 138 can be configured to retain the catheter tube 104 to the catheter hub 102. In one example, the bushing 138 can wedge the proximal end of the catheter tube 104 against the interior wall surfaces of the catheter hub 102 to retain the catheter tube 104 to the catheter hub 102.

The needle guard 132 may embody any number of prior art guards, tip protectors, or safety clips configured for blocking or covering the needle tip 110 of the needle 108. In the exemplary embodiment shown, the needle guard 132 can embody one of the guards shown in U.S. Pat. No. 6,616,630, the contents of which are expressly incorporated herein by reference. In one example, as shown in FIG. 5, the needle guard 132 can have a proximal wall 280 having a proximally facing wall surface and a distally facing wall surface with a perimeter defining an opening and two resilient arms 288, 290. The needle 108 can comprise a change in profile 144, which can be an attachment or sleeve, a crimp, or a bulge, for engaging the perimeter on the proximal wall of the needle guard 132 to retract the needle guard 132 in the proximal direction out of the catheter hub 102 following successful venipuncture, as further discussed below.

In the ready to use position, the proximal wall 280 may be in contact with a distal end 119 (FIG. 3. Of the needle hub 106, such as to a nose section, a tab, or a fin at a distal end of the needle hub. The two arms 288, 290 of the guard can intersect along a side view as described in U.S. Pat. No. 6,616,630 and shown in FIG. 5, or they can run along different sides of the needle and do not intersect along a side view. In one example, one arm can be longer than the other arm. Each arm 288, 290 can also include different sections of different arm widths, including a first arm section of a first width and a second arm section of a second width, which is smaller than the first width. The two arms 288, 290 can originate from different ends of the proximal wall 280 and can cross one another at their respective second arm sections. Thus, when viewed from a side along the lengthwise direction of the needle guard 132, the two arms intersect one another. When used with a needle 108, the two arms 288, 290 intersect one another when in a ready to use position and when in the protective position.

In an alternative embodiment, the two arms 288, 290 originate from different ends of the proximal wall and extend in a distal direction without crossing one another. Thus, the two arms 288, 290 can also have essentially the same arm width along the length of each respective arm. The needle guard 132 may be folded from a stamped metal sheet to form the guard as shown. Ribs 296 may be formed on the arms, the proximal wall, and/or distal walls to increase structurally rigidity. In some examples, the needle guard can be assembled from different components or parts and can include both metal and non-metal parts.

A distal wall 300, 302 can be provided at an end of each arm 288, 290. The distal walls 300, 302 on the two arms can overlap one another along an axial direction of the needle guard 132 when the arms close over the needle tip by utilizing different arm lengths and/or angling one of the walls at intersections with the resilient arms 288, 290 so that they are positioned serially along the length of the needle. The intersection between a distal wall and the elongated portion of an arm may also be referred to as an elbow or a diagonal diameter of the needle guard when referring to the two elbows on the two arms. In an example, an intersection or elbow 304 between the distal wall 300 and the resilient arm 288 can engage the guard engagement section 210 inside the catheter hub 102 to secure the needle guard 132 to the catheter hub 102 in the ready to use position, as shown in FIG. 3, and during the process of removing the needle 108 from the catheter hub 102, as shown in FIG. 4. Thus, the guard engagement section 210 can prevent the needle guard 132 from moving proximally before the needle guard 132 is activated to cover or block the needle tip 110 in the protected position. In some examples, the two distal walls of the needle guard can be called or be considered part of the two arms.

The needle guard arms 288, 290 can be biased outwardly by the needle shaft 109 in the ready position, as shown in FIG. 4, or by a pair of clip seats 235 of the valve opener 134, as discussed below with reference to FIGS. 13A-13C and 14A-14C and shown in FIG. 5. When the arms are biased outwardly, the radial profile of the needle guard increases. When the arms are not biased outwardly, the radial profile of the needle guard decreases, compared to when the arms are biased outwardly. The arms can be biased outwardly so that the intersections 304 of the two arms engage the guard engagement section 210 of the catheter hub 102 to retain the guard within the catheter hub in the ready to use position and during retraction of the needle following successful venipuncture. Said differently, the needle shaft 109 or the clip seats 235 of the valve opener 134 can apply an outward radial force on the lips or end surfaces 306 formed at the free ends of the two distal walls 300, 302 so as to urge the distal walls 300, 302, and the arms, outwardly to then engage the intersections 304 with the guard engagement section 210 of the catheter hub, or at least maintain the intersections 304 distal of the engagement section 210. In some examples, especially when the arms 288, 290 are only biased outwardly by the clip seats 235 of the valve opener 134 and not by the needle shaft, the engagement section 210 can be omitted or the intersections 304 can be situated inside the catheter hub without engaging the engagement section 210 of the catheter hub, as further discussed below. In still other examples, only one intersection of one of the arms is biased outwardly into engagement with the engagement section 210 of the catheter hub.

Referring now to FIG. 4, the lips 306 formed at the free ends of the distal walls 300, 302 and biased outwardly by the needle shaft 109 can create friction or drag as the needle 108 is withdrawn proximally following successful venipuncture and prior to needle guard activation. The lips 306 formed at the free ends of the distal walls 300, 302 can be rounded or curved to decrease drag on the needle shaft 109 during needle withdrawal. Alternatively, the lips 306 may be straight or not provided with the needle guard 132. In other examples, the distal walls are biased outwardly by the clip seats and no drag is generated between the needle shaft and the distal walls.

In an example, the needle guard 132 can be positioned inside a valve opener 134 or between two spaced apart structures of the valve opener so that no part of the free ends of the arms, at the ends of the two distal walls 300, 302, contact or are biased by the valve opener, as further discussed below. In other examples, the valve opener 134 can be sized and shaped so as to bias the two free ends of the needle outwardly. When the valve opener 134 biases the arms outwardly, the needle shaft does not have to also bias the two arms outwardly.

Referring now to FIG. 5, the valve opener 134 of the present embodiment is shown with an actuator head 150 and a pair of valve opener arms 152. The valve opener arms 152 can be spaced apart and can extend in the proximal direction from the actuator head 150, which can also be referred to as an actuator head or actuation end for pushing into a valve to open the valve, as further discussed below.

As shown, the two valve opener arms 152 are separated from one another by a width, which is larger than the diameter of the needle shaft but smaller than the width of the two free ends 306 of the needle guard. Consequently, the two free ends or lips 306 can press against part of the two valve opener arms 152, which can be called seat clips or arm seats 235, and be biased outwardly by the two valve opener arms. Thus, when the needle shaft is retracted from the catheter hub following vascular access, there is no drag or friction generated between the two free ends 306 of the needle guard 132 and the needle shaft 109.

With further reference to FIG. 5, during needle withdrawal, the change in profile 144 near the needle tip will eventually move proximally against the perimeter 282 defining the opening 284 on the proximal wall 280 of the needle guard 132. At this moment, additional proximal pulling force by the change in profile 144 on the proximal wall will overcome the engagement between the intersections 304 at the two arms of the needle guard 132 and the guard engagement section 210 of the catheter hub to retract the needle guard 132 proximally out of the catheter hub.

In one example, the additional pulling force can cause one or both arms 288, 290 of the needle guard 132 to elastically bend until the intersections 304 can slide through the clearance defined by the guard engagement section 210 and escape from the engagement. The clearance of the guard engagement section 210 can also be understood as the minimum interior dimension of the catheter hub. That is, the additional pulling force can be applied to cause one or both arms 288, 290 of the needle guard 132 to elastically deflect such that the radial profile of the needle guard 132 at the intersection is reduced to below the minimum diameter of the guard engagement section 210. After the lips 306 of both arms 288, 290 separate from the seat clips or arm seats 235, or from the two spaced apart valve opener arms, the needle guard 132 is activated to cover the needle tip 110. That is, the two distal walls can move to block the needle tip. In some examples, the guard engagement section 210 can be omitted and/or the intersections 304 do not engage the guard engagement section 210 in the ready position and during retraction of the needle following vascular access when free ends are biased outwardly by the valve opener.

Referring back to FIGS. 3 and 8, the guard engagement section 210 can be formed in the interior cavity 130 of the catheter hub 102 to hold the needle guard 132 in the ready to use position and during needle withdrawal, such as when the arms of the needle guard 132 are biased outwardly by the needle shaft 109. The guard engagement section 210 can extend radially inwardly into the interior cavity of the catheter hub 102 to form a minimum diameter inside the catheter hub. The guard engagement section 210 can have an interference overlap with the diagonal diameter of the needle guard 132, such as the two intersections 304 of the two arms, to ensure the needle guard 132 is secured in place inside the catheter hub in the ready to use position and during retraction of the needle. A tapered or slanted surface at the two intersections 304 can decrease the pulling force required to disengage the needle guard 132 from the guard engagement section 210 of the catheter hub 102.

The needle guard 132 can be assembled inside the interior cavity 130 of the catheter hub 102 by pushing the proximal wall 280 of the needle guard 132 with the distal end of the needle hub 102 as the needle hub 102 with needle 108 is inserted into the catheter hub 102. In the ready to use position, the needle guard 132 can extend at least partially into a gap 154 (FIGS. 11A, 12A) of a valve opener 134 with the proximal section of the needle guard 132, such as the proximal wall 280, located outside or proximal of the valve opener 134. That is, the proximal wall 280 of the needle guard 132 can be located proximally of the proximal end surfaces 151 of the valve opener 134. In another example, the proximal wall 280 of the needle guard 132 can be flush or coplanar with the proximal end surfaces 151 of the valve opener 134. In yet another example, the proximal wall 280 of the needle guard 132 can be located distally of the proximal most surfaces of the valve opener 134. In embodiments in which the valve opener 134 biases the two arms outwardly, the distal walls of the two arms either do not fit within the gap 154 of the valve opener or the valve opener is provided with seat clips or arm seats 235 to support the two distal walls, as further discussed below.

When the needle tip 110 is pulled into the needle guard 132 following successful venipuncture, the change in profile 144 on the needle 108 engages a perimeter 282 defining an opening 284 on the proximal wall 280 of the needle guard 132, as previously described. At this moment, the arms 288, 290 of the needle guard 132 may simultaneously or soon thereafter, collapse to their protective position to block accidental contact with the needle tip 110 when clear of the needle shaft 109 or the clip seats 235 of the valve opener 134. The same working can also be achieved by one of the one arm needle guards described in U.S. Pat. No. 6,616,630, which runs along a side of the needle shaft instead of crossing the needle as shown in some of the embodiments of the '630 patent.

With reference now to FIG. 6, after the needle hub 106 and needle 108 are withdrawn from the catheter hub 102 and the needle tip 110 is secured by the needle guard 132, the valve opening 324 of the valve 136 can reseal upon itself to prevent or limit blood or other fluid from passing through the valve opening 324. That is, after withdrawal of the needle shaft 109 from the valve opening 324, the potential elastic energy stored in the valve 136 generated from the needle shaft 109 deflecting the flaps of the valve 136 surrounding the valve opening 324 is released and the flaps return to a less deflected or closed position to reseal the valve opening 324. Thus, FIG. 6 shows the needle 108 completely removed from the catheter hub 102 and the valve opener 134 ready to be pushed by a male Luer tip distally against the proximal end surfaces 151 of the valve opener 134 to advance the valve opener against the valve 136 to open the valve 136.

The catheter hub 102 can be designed such that an engagement distance "A" between the proximal end 122 of the catheter hub 102 and the proximal end surfaces 151 of the valve opener 134 may be less than or equal to the minimum length of engagement of a male medical implement, such as a syringe tip or a male Luer fitting, into the catheter hub 102. This can ensure that in the event of a connection of a male lock fitting, the male lock fitting would introduce a longitudinal force onto the valve opener 134 and allow a longitudinal displacement of the valve opener 134 towards the proximal end of the valve 136 to open the valve 136. In one example, the engagement distance is per ISO standard, as presently established or established in the future.

The catheter hub 102 can also be designed such that a minimum depth "B" of the interior cavity of the catheter hub 102 from the proximal end 122 of the catheter hub 102 may be greater than or equal to the minimum length of the male lock fitting to ensure that in the event of a connection of a male lock fitting, the male lock fitting would have sufficient surface contact area with the female Luer taper at the proximal opening 121 of the catheter hub 102.

FIG. 7 shows a male medical implement 50, such as a male Luer lock or a syringe tip, inserted into the interior cavity 130 of the catheter hub 102 through the proximal opening 121 at the proximal end 122 of the catheter hub 102 to displace the valve opener 134 in a distal direction to press against the valve 136 to open the valve 136. In one example, when a male Luer lock fitting is attached from the proximal end 122 of the catheter hub 102, the male Luer lock fitting will contact the valve opener arms 152. As the lock fitting is threaded with the exterior threads at the proximal end 122 of the catheter hub 102, the male fitting pushes against the proximal end surfaces 151 of the valve opener arms 152 distally until the head 150 of the valve opener pushes the valve 136 open.

When the valve 136 opens, fluid can pass through the valve opening 324 of the valve. When the lock fitting 50 is subsequently removed, the valve 136 can elastically recover back to reseal the valve opening 136. As the valve 136 reseals itself, the valve 136 can stop or limit flow through the opening while simultaneously push the valve opener 134 proximally back to its ready to use position or its proximal position of FIG. 6 thereby allowing multiple use of the blood control system.

In an example, the actuator head 150 has a frusto-conical shape so as to readily deflect the flaps of the valve in the distal direction to open the valve. The valve flaps of the valve 136 may be made sufficiently resilient, such as by making the flaps thicker, so as to return to its closed position after the male Luer tip 50 is removed and an axial load is no longer applied to the valve actuator. In another example, an elastic element, such as a resilient gasket or a spring, may be incorporated to assist with closing the flaps on the valve. The frusto-conical shape of the actuator head 150 can retain a proximally directed force vector of the flap against the conical surface, which can push the actuator back to its starting position until the flaps are closed again and flow is stopped. Various embodiments of the valve opener 134 and various embodiments of the valve 136, which may be implemented in the blood control system, are further discussed below.

FIGS. 11A-11C show an isometric view, a top view, and a profile view, respectively, of a valve actuator or valve opener 134 in accordance with aspects of the present disclosure, which can be used with catheter assemblies described elsewhere herein and in a similar manner as the valve opener described with reference to FIGS. 5-7. The valve opener 134 can comprise an actuator head 150 and at least one valve opener arm 152, such as a leg element or an elongated extension. In an exemplary embodiment, two valve opener arms 152 can extend from the head 150 in the proximal direction and each can have a length measured in a lengthwise direction of the catheter assembly and a width, measured orthogonally to the length. As shown, the two valve opener arms 152 are spaced apart and extending from opposite points or sections of the head 150. The two valve opener arms 152 can be sized and shaped for contact by a male Luer to transfer a distally directed force from the male Luer to the head 150 to then push against the valve 136 to open the valve 136, as further discussed below.

A bridge or stabilizer element 155 connected to the two valve opener arms 152 can add rigidity to the two valve opener arms 152 and provide additional surface area for contact with the male Luer. The bridge 155 can extend from an outer edge of one valve opener arm 152 to an adjacent outer edge of the other valve opener arm 152 to connect the two valve opener arms 152 together without impeding fluid flow through the valve opener 134 or interfering with the needle 108 or the needle guard 132, which can be located between the two valve opener arms 152 in the ready to use position. As shown in FIGS. 11A-11C, the outer surfaces of the two valve opener arms 152 and the bridge 155 can be arc shaped and piecewise continuous to form a semi-circular shaped cross section along a width or radial direction of the valve opener. In an example, proximal surfaces 151 of the valve opener arms 152 and a proximal surface 157 of the bridge 155 can be coplanar. In other examples, the proximal surface 157 of the bridge 155 can locate distally of the proximal surfaces 151 of the two valve opener arms.

In some examples, the outer surfaces of the two valve opener arms can also be tapered in the lengthwise direction to match a taper of the interior cavity of the catheter hub 102. In one example, the two valve opener arms taper inwardly from the proximal surfaces 151 of the valve opener arms 152 to match the female Luer taper at the proximal end of the catheter hub 102. The bridge 155 can extend a short distance in the distal direction to provide a through opening or through hole 54 cooperatively defined between the bridge 155, the two valve opener arms 152, and the head 150. The through opening 54 can be provided to enable an intersection 304 of one of the arms of the needle guard to project therethrough to engage the guard engagement section 210 of the catheter hub. Alternatively or additionally, the intersection 304 can engage the distal edge of the bridge 155 to retain the guard in the ready to use position and during retraction of the needle. In some examples, the bridge 155 can extend to the head 150 and no through opening or through hole is provided between the two valve opener arms and the bridge. The thickness of the bridge 155 can be sufficiently thin such that during assembly, at least one of the arms 288, 290 of the needle guard 132 can elastically deform to move pass the bridge 155 along the longitudinal axis without causing permanent deformation or damage to the needle guard 132 during assembly and during activation of the needle guard.

The thickness of each of two valve opener arms 152 can be sufficiently small or thin so that the needle guard 132 and the two valve opener arms 152 have sufficient clearance to fit within the interior cross-sectional space of the catheter hub 102 without being physically binding against the catheter hub 102 and rendered unmovable or fixed. In an example, the thickness of each of two valve opener arms 152 and the width of the needle guard are such that no undercut or channel is required to be formed in the interior wall surfaces of the catheter 102 hub to accommodate them. When the valve opener arm 152 has an arc cross section, it may be structurally stronger to handle a greater load when being pushed by a male tip to push the head 150 against the valve 136. This can allow a thin and compact design for the infusion device and gives more room in the standardized space of a female Luer taper.

The valve opener 134 can be made from a metal material or from a polymer material. When made from a metal material, the valve opener 134 can be formed by deep draw methods or punching or cutting a pattern from a sheet metal and bending the stamped or cut pattern to form features of the valve opener 134 including the head 150 and the at least one valve opener arm 152. The at least one valve opener arm 152 can be bent further to form an arc-shaped cross section to provide added rigidity when pushed by the male Luer. In one example, the valve opener 134 is formed from a stamped stainless steel pattern worked into a desired shape. When made from a polymer material, the valve opener 134 can be molded as a single piece. In some examples, the valve opener can be co-molded or insert molded to form surface features and/or to incorporate different materials. In one example, the polymer material can be a high-strength semi-rigid or rigid material.

Each valve opener arm 152 can comprise at least two lengthwise flanges 200 and a recessed channel defining a drain 212 between the two flanges 200 at an interior surface 153 of each of the two valve opener arms 152. The two flanges 200 on each arm can have equal widths with unequal widths contemplated. The width of the channel defining the drain 212 can be the same as or different from the width of the flanges 200. The drains 212 are optional and when incorporated can provide additional flow space for fluid flow along the length of the valve opener, between the two valve opener arms 152.

With further reference to FIG. 11A, the gap 154 between the two arms 152 can provide clearance or space for fluid flow flowing thereacross, such as during IV infusion, and accommodate a needle guard 132. The structural rigidity of each valve opener arm 152 remains relatively the same when the drains 212 are incorporated but can increase the fluid flow space beyond the gap 154.

An undercut 205 can be formed on the exterior circumference of the valve opener 134 and can be located on the exterior of the valve opener arms 152. The undercut 205 can be sized, shaped, and located on the valve opener so that it seats distal of the guard engagement section 210 or so that the guard engagement section 210 can secure the valve opener 134 within the interior of the catheter hub from displacing proximally out of the catheter hub. The configuration of the undercut 205, such as the curve, the dimension, the width, the height, etc., can be selected to allow easy axial displacement of the valve opener 134 towards the valve 136 and back and be retained by the guard engagement section 210. The undercut 205 can have two sidewalls 206 separated by a bottom surface 207, similar to a recess or groove. The two sidewalls 206 can be perpendicular to the bottom surface 207 or tapered outwardly to form an opening wider than the width of the bottom surface. The depth of the undercut 205 can allow the valve opener 134 to slide freely. The amount of axial displacement can be limited by the width of the bottom surface 207 or the sidewalls 206 interacting with the guard engagement section 210. The shape of the undercut 205 and its relative position to the guard engagement section 210 can also cause the actuator head to contact and/or provide a slight axial load against the proximally facing surface of the valve even when the valve opener is not axially loaded or pushed by a male Luer tip.

The actuator head 150 of the valve opener 134 can comprise a body 158 with an outer perimeter 160. In an example, the outer perimeter 160 can be generally rectangular with two opposing flat surfaces 161 that align with the opening of the gap 154. The perimeter 160 further comprises two opposing arc-shaped side surfaces 162, which are continuous with the arc-shaped surfaces of the valve opener arm 152. In other examples, the outer perimeter 160 can have a taper extending outwardly from a distal end to a proximal end to form a wedge. Interiorly, the body 158 can comprise a through opening 164 formed through the head 150 and in fluid communication with the gap 154 to allow fluid to pass through the valve opener 134. The drains 210 of the valve opener arms 152 can extend through the head 150 and form part of the through opening 164. Thus, fluid can pass through the opening 164 as well as around the head 150 over the flat surfaces 161. If the bridge 155 extends from the proximal surfaces 151 of the valve opener arms 152 to the head 150 without a through opening 54, such as a full length bridge, fluid can be forced to pass through the opening 134 and around a single flat surface 161, on a side opposite the full length bridge.

In an alternative embodiment, the distal side or surface of the actuator head 150 of the valve opener 134 can include a taper or frusto-conical nose section to facilitate opening the valve, such as to deflect the flaps of the valve.

FIGS. 12A-12C show an isometric view, a top view, and a profile view, respectively, of a valve actuator or valve opener 134 in accordance with another aspect of the present disclosure. The valve opener 134 of the present embodiment can comprise a head 150 and a pair of valve opener arms 152, which may also be referred to as leg elements or elongated extensions, extending in a proximal direction, either directly or indirectly, from the head 150. The valve opener 134 shares similar aspects with the valve opener 134 of FIGS. 11A-11C, except that the head 150 is shaped differently to generate a different deflection on the valve 136 to open the valve and to aid in retracting the valve opener 134 proximally when the male medical implement is removed, which allows the valve 136 to close. The present valve opener is also without any bridge. Additionally, a pair of guide tabs 159 extending from opposite sides of the valve opener 134, such as radially of the two valve opener arms, to restrict movement of the valve opener to an axial direction within a limited range. For example, the guide tabs 159 can cooperate with the slots 135 (FIG. 8) in the interior cavity of the catheter hub to confine movement of the guide tabs therein and hence movement of the valve opener. Further, upon insertion of the valve opener into the catheter hub during installation of the valve opener, the guide tabs can create a sound, such as a click, to provide feedback. The shape of the guide tabs 159 and their relative positions to the slots 135 can also cause the actuator head 150 to contact and/or provide a slight axial load against the proximally facing surface of the valve even when the valve opener is not axially loaded or pushed by a male Luer tip.

With reference to FIG. 12B, the two valve opener arms 152 are attached at their respective distal ends to base members 56 of the actuator head 150. Each base member has a tapered surface 221 along the interior and a tapered surface 221 on the exterior, relative to the gap 154 located in the interior. As shown, the guide tabs 159 extend from the exterior tapered surfaces 221. In a particular example, the guide tabs 159 are located at the proximal ends of the two exterior tapered surfaces 221.

The head 150 further comprises a generally flat rectangular frame 220 having two lengthwise edges 220a, 220b extending elevation-wise above and below the edges of the two arms 152 and having a through opening 164 for needle access and for fluid flow. Two distally directed projections 223 can extend from the generally flat rectangular frame and having the through opening 164 located therebetween. In some examples, the exterior tapered surfaces can extend continuously to the distal ends 223a of the two distally directed projections 223 to form actuating projections on the head 150 to push open a valve.

In an example, the distal ends 223a of the distally directed projections 223 have a generally flat or planar surface. In other examples, the distal ends 223a can be rounded or arcuate. The arcuate shaped distally directed projections 223 can maintain a pair of component forces when pushed against the resilient flaps of the valve, which allow the flaps to return to their more relaxed positions when no longer pushed by the valve opener.

As previously described, guide tabs 159 are provided to guide the valve opener within the catheter hub. The guide tabs 159 can each have a width that extends between the edges of the respective valve opener arm. In other examples, the widths of the guide tabs are substantially the same as the widths of the arms. Optionally, the widths can be smaller. As shown in the top view of FIG. 12B, the guide tabs 159 and the head 150 resemble a U-shape structure with two projections 223 extending axially of the head and having a through opening 164 located therebetween for needle access and fluid flow.

The guide tabs 159 are configured to slide axially back and forth inside the horizontal slots 135 (FIG. 8) formed in the interior cavity of the catheter hub 102 when the valve opener 134 is mounted therein. The horizontal slots 135, having a defined length, can guide the guide tabs 159 of the valve opener 134 and restrict the range of axial displacement. Each horizontal slot 135 can embody an undercut with a length extending along the axial direction and sized to at least allow the valve opener 134 to slide axially to open the valve 136 and to return proximally with the valve 136 closed. The horizontal slots 135 can each have a width larger than a width of the guide tabs 159 and have a depth greater than the outside dimension measured between the two outermost radial points of the guide tabs 159 to prevent the guide tabs 159 from binding or seizing in the horizontal slots 135.

The gap 154 is sized to accommodate the needle guard 132, which can fit between the valve opener arms 152. As shown in FIGS. 12A-12B, the gap 154 extends between the valve opener arms 152 and tapers at the base members 56. The tapered portion of the gap 154 can be determined by the tapered surface 221 along the interior. In some examples, the size of the two base members and angle of the tapered surface 221 along the interior can be selected so that the curved lips at the ends of the two distal walls of a needle guard, or the edges of the distal walls if no curved lips are incorporated, rest on the upper and lower planar surfaces 56a, 56b of the base members 56, which can act to bias the two arms outwardly instead of the needle shaft biasing the two arms outwardly, as discussed above with reference to FIG. 5. Optionally, the two curved lips or the distal walls if no curved lips are incorporated can be located proximally of the two base members 56 so that the needle biases the two arms outwardly, as discussed above.

A drain 212 can be located between the two flanges 200 on each valve opener arm 152 and extends from the proximal surface 151 of the arm to the tapered portion of the gap 154, similar to the drain 212 discussed above with reference to FIG. 11A. Optionally, the drain 212 can be omitted from one or both valve opener arms 152.

FIGS. 13A-13C show an isometric view, a top view, and a profile view, respectively, of a valve actuator or valve opener 134 in accordance with yet another aspect of the present disclosure. The valve opener 134 can comprise a head 150 and a pair of valve opener arms 152, such as a pair of leg elements or elongated extensions, extending in the proximal direction from the head 150. The valve opener 134 is similar to the valve opener 134 of FIGS. 12A-12C with a few exceptions. In the present embodiment, the head 150 can have a proximal surface that is generally flat and the structure that extends from the proximal surface can have a frusto-conical shape. Additionally, a clip seat 235 can extend from the interior surface 153 of each valve opening arm 152. The clip seat 235 can be configured to support the distal walls or lips at the end of the distal walls of the needle guard 132 so that the arms of the needle guard 132 seat against the clip seat 235 instead of the needle shaft 109 in the ready to use position and during needle withdrawal. The frusto-conical shaped head 150 can have a flat circular front surface 230 transverse to the needle axis at a distal end of the head 150 and a conical tapered surface 231 extending proximally and outwardly from the flat circular front surface 230 to form a conical wedge. The conical shape of the head 150 can assist the valve opener 134 to push open the valve 136 and retract proximally upon the valve 136 closing.

The clip seat 235 can extend from the interior surface 153 of each valve opening arm 152 into the gap 154. The height of the clip seat 235 measured from the interior surface 153 of the valve opener arm 152 towards the center of the gap 154 can vary along the valve opener arm 152 so long as the needle 180 can extend between the clip seats 235. The gap between the two clip seats 235, however, is smaller than the width of the two distal walls of a needle guard so that the distal walls, or the lips at the ends of the distal walls, can press against the clip seats and bias outwardly by the clip seats. As shown, in FIG. 13B, each clip seat 235 can have a wide base 235a that extends further into the gap 154 and an elongated body 235b that extends less into the gap 154 than the base. The two wide bases 235a of the two clip seats 235 therefore define a narrow portion or minimum portion of the gap 154 located between the two valve opener arms 152.

In one example, a clip seat 235 is formed between the head 150 and about the midpoint of the length of each valve opener arm 152. The clip seat 235 can narrow the gap 154 and form a transition region to the circular opening 164 extending through the head 150. Viewed from a top view as shown in FIG. 13B, the gap 154 extends between the valve opener arms 152 at the proximal end and begins to converge at a mouth region located at about the midpoint of the valve opener arm 152 to a throat region before it gradually diverges to the circular opening 164. Said differently, the gap 154 extends from the proximal end of the valve opener arms 152 to a transitioning region defined by the clip seats 235 extending from the interior surfaces 153 of the valve opener arms 152 at a distal portion of the valve opener arms 152. The transitioning region, when viewed from a top view as in FIG. 13B, can resemble a nozzle. The throat region of the nozzle can support the arms of the needle guard 132.

The thickness of the clip seat 235 can be the same or larger than the outer diameter of the needle 108 so that the safety clip arms seat on an opposite engaging surfaces of the clip seats 235. Different size needles can be used so long as the thickness of the clip seat is larger than the outer dimeter of the various needles. This allows a uniform valve opener 134 to be used for different needle sizes, such as for a range of needle diameters, and for the valve opener to bias the arms of the needle guard rather than the needle shaft. Thus, the same valve opener can be used for different needle sizes or a range of needle diameters, such as for needle sizes from G18 to G24. The range is understood to mean that a particular needle shaft diameter can be a 18 gauge needle and can fall into or within a range of needle diameters, such as a needle range of 18 gauge to a 24 gauge needle. In other examples, the range can be greater, such as 14 gauge to 24 gauge. An additional advantage to harmonizing the same valve opener across several different needle sizes is the predictability of the diagonal diameter of the needle guard when biased outwardly by the clip seats and/or the valve opener arms. This in turn allows for the same minimum inside diameter of the catheter hub, assuming a clip engagement projection is incorporated for engaging the needle guard. The clip seats 235 can also add structural rigidity to the valve opener arms 152. Edges of the clip seat 235 may be chamfered, curves, or smoothed to allow easy assembly of the needle guard 132.

With particular reference to FIGS. 13A and 13B, a guide structure 159 can be formed on an exterior of each valve opener arm 152 just proximal of the conical tapered surface 231. The guide structure 159 can form by extending the conical tapered surface 231 of the head and a sharp transition or indentation to define a shoulder on the exterior of each arm 152. Said differently, the proximal end of the conical tapered surface 231 of the head can have an outside diameter of a first dimension and the two valve opener arms 152 can define an outside diameter of a second dimension, which is smaller than the first dimension, to define the two guide structures 159. The first dimension can be larger than the circumference of the projection 210 in the interior cavity of the catheter hub 102. The guide structure 159 can be provided between the two different dimensions on each arm. Alternatively, the guide structures 159 can extend outwardly anywhere along a length of the valve opener 134 from opposite sides of the valve opener 134.

With continued reference to FIGS. 13A and 13B, the first dimension at the proximal end of the conical tapered surface 231 of the head can be around 10% to 40% smaller than an outer diameter of the valve 136 to ensure that the head of the valve opener 134 would not pass fully through the slits of the opened valve 136 when a male Luer fitting advances the valve opener. This would therefore allow the valve opener 134 to return or retract proximally upon removal of the male Luer and the valve 136 closing, thus allowing multiple use of the blood control system. Alternatively, the valve opener can be sized and shaped so that the guide structures 159 can pass through the opened valve and be stuck distally of the valve 136 making the valve and valve opener a one-time use blood control device. As shown in the top view presented in FIG. 12B, the guide structures 159 and the head cooperatively form an arrow like structure with a truncated tip.

Horizontal slots 135 can be provided inside the interior cavity 130 of the catheter hub 102 distal of the guard engagement section 210 to guide the valve opener 134 in the axial direction inside the interior cavity 130, as previously described with reference to FIG. 8. That is, the guide structures 159 of FIGS. 13A-13C are configured to slide axially back and forth inside the horizontal slots 135 formed in the interior cavity 130 of the catheter hub 102. The shape of the guide structures 159 and their relative positions to the slots 135 can also cause the actuator head 150 to contact and/or provide a slight axial load against the proximally facing surface of the valve even when the valve opener is not axially loaded or pushed by a male Luer tip.

FIGS. 14A-14C show an isometric view, a top view, and a profile view, respectively, of a valve actuator or valve opener 134 in accordance with still yet another aspect of the present disclosure. The valve opener 134 can comprise a head 150 and a pair of valve opener arms 152, such as a pair of leg elements or elongated extensions, extending from opposite sides of the head 150. The valve opener 134 of the present embodiment shares many similar aspects as the valve opener 134 of FIGS. 13A-13C with a few exceptions. In the present embodiment, the thickness of each of the valve opener arms 152 is the same as the clip seats 235, which is greater than or equal to the outer diameter of the needle shaft 109 so that the arms of the needle guard 132, such as the curved lips or distal walls, seat on the engaging surfaces of the clip seats 235 rather than the needle shaft 109. Said differently, the valve opening arms 152 have a thickness greater than or equal to the outer diameter of the needle shaft 109, with engaging surfaces on opposite sides of the valve opener arms 152 to support the arms of the needle guard 132 in the ready to use position. The valve opener arms 132 cooperatively define a gap 154 from a proximal end of the valve opener arms 152 to the head 150. The gap 154 can expand at about the midpoint of the valve opener arm 152 to the circular opening 164 extending through the head 150.

A ridge 240 can be provided on a surface of the valve opener arm 152, or two ridges on each arm, to catch the safety distal walls of the needle guard 132 to secure the needle guard 132 in the ready to use position or during needle withdrawal prior to activation of the needle guard 132. Thus, the one or more ridges 240 can act as a guard engagement section to retain the needle guard 132 to the valve opener, in which case the guard engagement section 210 of the catheter hub may be omitted. Said differently, a guard engagement section can be formed on the clip seat 235 of the valve opener 134 to allow at least one of the arms of the needle guard 132 to engage the valve opener 134 in the ready to use position and during retraction of the needle following successful venipuncture instead of engaging the guard engagement section 210 formed on the interior cavity 130 of the catheter hub 102.

The ridge 240 may be a protrusion with a rounded or arc shape extending from a surface of one or both valve opener arms 152. The proximal end surfaces 151 of each valve opening arms 152 may also be rounded. The shape of the guide tabs 159 on the two valve opener arms 152 and guide tabs' relative positions to the slots 135 can also cause the actuator head 150 to contact and/or provide a slight axial load against the proximally facing surface of the valve even when the valve opener is not axially loaded or pushed by a male Luer tip. In an example, the guide tabs 159, the two valve opener arms 152, and the two clip seats 235 are formed continuously with a same width. In other examples, the guide tabs 159 can have a different width than the valve opener arms and the clip seats.

Figures 15A, 15B, 15C:
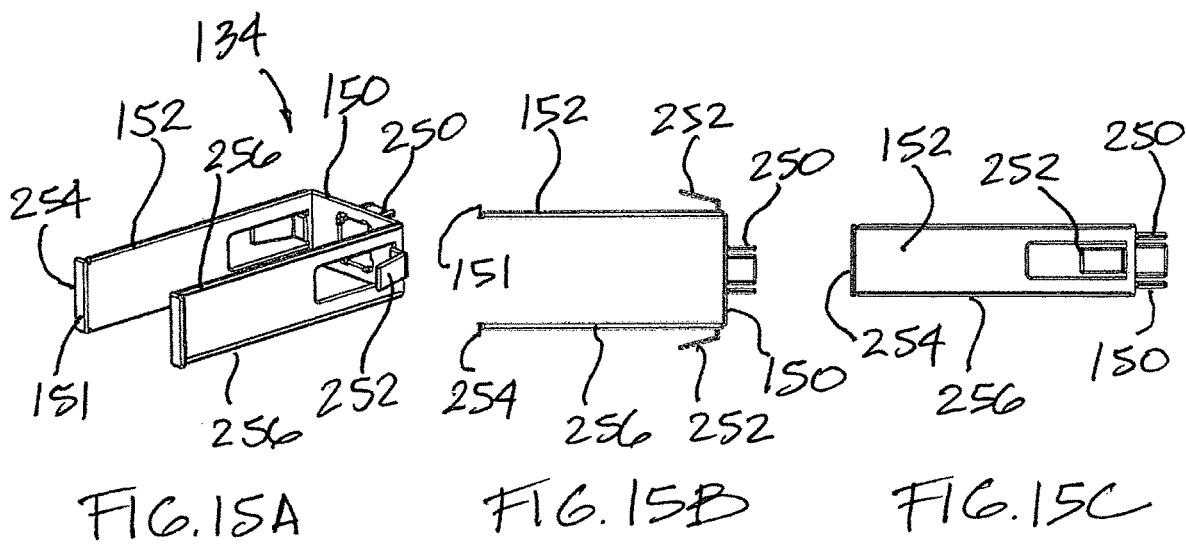
FIGS. 15A-C show an isometric view, a top view, and a profile view, respectively, of still yet another embodiment of a valve actuator in accordance with aspects of the present disclosure.

Although valve openers 134 can be formed or made by plastic injection molding, such as the valve openers of FIGS. 11A-14C, valve openers described herein can also be made from a metal material. FIGS. 15A-15C show an isometric view, a top view, and a profile view, respectively, of a valve actuator or valve opener 134 in accordance with still yet another aspect of the present disclosure. The valve opener 134 can comprise a head 150 and a pair of valve opener arms 152, such as a pair of leg elements or elongated extensions, extending from opposite sides of the head 150. The valve opener 134 of the present disclosure can be formed from a stamped sheet metal and then bent to form features of the valve opener 134 including the head 150 and a pair of valve opener arms 152 extending proximally from opposite sides of the head 150.

Fingers 250 can extend distally from a center portion of the head 150 that together can define a distal projection having a through passage therebetween. The fingers 250 can form by slitting the surface of the head and then bending the tabs to create fingers that define the distal projection. In an example, there can be four fingers 250 that can form a generally square or rectangular projection. The fingers 250 can act as an opening member to push open the valve 136 when the valve opener 134 is pressed distally into the valve 136 by a male Luer fitting. The shape and number of fingers can vary.

Side wings 252 can extend outwardly and transversely from outside surfaces of the valve opener arms 152. The side wings 252 can extend transversely from the valve opener arms 152 to form an angle greater between zero degrees and 90 degrees to allow the valve opener 134 to snap-fit into the horizontal slots 135 (FIG. 8) of the catheter hub 102. Thus, the side wings 252 are similar to the guide structures 159 on other valve openers described elsewhere and can extend outwardly anywhere along a length of the valve opener 134 of the present embodiment from opposite sides of the valve opener 134.

A proximal flange 254 can extend outwardly along the transverse axis from the proximal end surface 151 of each valve opener arm 152 to provide additional surface areas for the male Luer conical fitting to press against to push the valve opener in the distal direction to open the valve. Arm flanges 256 can extend outwardly and transversely on opposite lengthwise edges of the valve opener arms 152 to increase the structural rigidity of the valve opener arms 152. In some examples, the surface of the opener arms 152 can be worked to for a curved shape, such as an arc shape, to increase the strength of the arms against axial load by the male Luer tip.

With reference now to FIGS. 9A and 9B, a cross-sectional side view and an isometric view of an exemplary valve 136 provided in accordance with aspects of the present disclosure are shown. The valve 136 may be usable with the catheter assemblies and hubs with a female Luer described elsewhere herein. The valve can be called or considered a disc valve. The disc valve can optionally include one or more flanges extending therefrom, as further discussed below. The valve 136 is shown with a valve body 320 having a width measured from one edge to another edge of an outer perimeter or outer diameter 322 of the valve body 320. The valve body 320 has a thickness, which is the dimension that extends orthogonal to the width from a first surface 327*a* to a second surface 327*b*. The valve 136 can be seated in a valve seating area or valve groove 137 (FIG. 8) provided in the interior cavity of the catheter hub 102. The valve is configured to be located distal a valve opener 134 to form a seal in the interior cavity and to be opened by the valve opener.

The valve groove 137 can be a radial undercut formed in the interior cavity of the catheter hub 102 with a depth in the range between about 0 mm to about 1 mm deep, or recessed, to allow proper seating. The depth range can have a tighter tolerance of about 0 mm to about 0.3 mm. A seal is provided between the interior of the catheter hub 102 and the outer surfaces of the valve 136 such as the outer perimeter 322. In one example, a slight compressive force can be applied by the catheter hub against the perimeter of the valve to ensure sealing. Alternatively or in addition, the outer edges of the first and second surfaces 327*a*, 327*b* can seal against the surfaces of the valve groove 137 to provide a seal with the catheter hub. In an example, the profile of the valve groove 137 as well as any profile internally of the catheter hub, such as slots or projection(s), can be contoured with radiuses to minimize smearing of material during the molding process of the catheter hub.

A valve opening 325 (FIG. 6) can extend through the thickness of the valve body 320 from the first surface 327*a* to the opposite second surface 327*b*. The thickness of the valve body 320 can be uniform or can vary. The thinner the valve 136, the less resistance the valve 136 is to opening, and therefore less force is required to open the valve 136. The thicker the valve, the more elastic energy is able to be stored to enable the valve to return to its original pre-opened shape upon elastic deformation, and thus allowing multiple access of the valve opening and closing. In one example, the thickness of the valve is in the range of about 0.3 mm to about 1.5 mm. However, the thickness can vary and can include other ranges.

A first flange 323a can extend axially from the outer perimeter or outer diameter of the valve body 320 to allow better seating of the valve in the catheter hub 102. The first flange 323a can be oriented in the catheter hub to extend proximally as shown in FIG. 1 or distally. The first flange 323a and the valve body 320 can cooperatively define a first circular cavity 328a concentric with the valve body 320 and locally reducing the thickness of the valve 136 at the first circular cavity 328a.

The valve opening 324 is shown with three slits extending radially from a center of the valve 136 and formed approximately 120 degrees apart, thereby forming a first flap 326a, a second flap 326b, and a third flap 326c. That is, the three slits can intersect at a single central point 329 coinciding with the axis of the valve 136. The length of the slits can vary. In one example, the slits extend to the first flange 323a. The first flap 326a, the second flap 326b, and the third flap 326c can be deflected to open a flow path 226 through the valve body 320. The fluid flow path 226 is provided when the three flaps are deflected by the valve opener. In an example, the flaps 326a, 326b, 326c near the central point 329 expand radially towards the perimeter 322 and in the distal direction when deflected by the valve opener 134. That is, the first flap 326a, the second flap 326b, and the third flap 326c can be deflected by pushing the valve 136 with one of the valve openers 134 described herein on a proximal side of the valve 136, as discussed further below.

Alternatively, the valve opening 324 can be a single slit 324 formed through the thickness of the valve body 320 and defining a first flap and a second flap, which can also be deflected to open a flow path through the valve body 320 by pushing the valve 136 with a valve opener 134 on one side of the valve.

In an example, the valve opening 324 may also include reliefs embodying two short through cuts at each end of the slit forming a V-shaped relief. The reliefs can provide clearance for the flaps to enable them to deflect more readily when pushed open by the valve opener 134. Less preferably, a single short through cut may be incorporated at each end of the slit.

Referring to FIG. 9B, a second flange 323b can extend axially from the outer perimeter of the valve 136 opposite the first flange 323a thereby cooperatively forming a second circular cavity 328b concentric with the valve body 320 and further reducing the thickness of the valve 136 at the first and second circular cavities 328a, 328b.

FIGS. 10A and 10B are a cross-sectional side view and an isometric view, respectively, of an exemplary valve 136 provided in accordance with further aspects of the present disclosure, which may be usable with the catheter assemblies and hubs with a female Luer described elsewhere herein. The present valve 136 is similar to the valve of FIGS. 9A-9C with a few exceptions. In the present embodiment, the valve 136 has a circular valve body with a varying thickness that increases from a central point of the valve 136 towards the outer perimeter 322 of the valve 136. The thickness can vary linearly with a constant slope or can have a complex slope. The valve 136 has an opening 324 with three slits 324 provided through the thickness of the valve body 320 to form three flaps 326a, 326b, 326c. The three slits 324 can intersect at a single central point 329 coinciding with the axis of the valve 136. The flaps can be deflected to open a flow path 226 through the valve body 320. The first, second and third flaps 326a, 326b, 326c can be deflected by pushing the valve 136 with a valve opener to deflect the flaps radially and axially. A fluid flow path 226 can be provided when the three flaps are deflected. In an example, the flaps 326a, 326b, 326c near the central point 329 expand radially towards the outer perimeter 322 and in the distal direction when deflected by the valve opener 134 pressing against the proximally facing surface of the valve 136.

With reference again to FIG. 3, the valve 136 can be located inside the catheter hub 102 just distal of the head 150 of the valve opener 134. The valve 136 can comprise an outer perimeter that can be seated in a valve groove 137 (FIG. 8) to fix the outer perimeter of the valve 136 between the valve opener 134 and the bushing. Alternatively, the outer perimeter of the valve 136 can be fixed to the interior cavity of the catheter hub 102 between the valve opener 134 and the bushing 138 by interference fit, adhesive, or other securing means.

FIG. 6 shows the needle 108 completely removed from the catheter hub 102 with the needle guard 132 (FIG. 3) covering the needle tip 110 in a protective position, which is not shown but is understood in the relevant art. To get to this position, the needle device 100 starts at the position of FIG. 3, which may first require removal of a disposable protective cap, moves to a transition position of FIG. 4 wherein the needle slides proximally relative to the catheter tube and the catheter hub, and then continuing to move the needle until the needle tip 110 moves proximally of two distal walls 300, 302, one on each end of the resilient arms 288, 290 of the needle guard 132. The distal walls can be considered part of the arms on the needle guard and are specifically called out so as to identify the structure and function in relations to the other components and how the disclosed needle assemblies operate.

Where the needle guard 132 has only one distal wall and/or one arm, the process is similar but the needle tip only has to move proximally of the one distal wall to cause the needle guard to activate. As the two distal walls and hence the two resilient arms 288, 290 are no longer biased outwardly by the needle 10 or valve opener 134, the two arms 288, 290 move radially to decrease the guard's radial profile and to disengage from the guard engagement section 210 of the catheter hub 102. Alternatively, the one arm and one distal wall can disengage from the one guard engagement section 210.

Where the arms of the needle guard are biased outwardly by the clip seats of the valve opener, the arms remained biased until the change in profile on the needle moves proximally and contacts the perimeter on the proximal wall of the needle guard. Further movement of the needle from that point moves the proximal wall, and hence the entire needle guard, in the proximal direction until the distal walls separate from the clip seats on the valve opener, or from the valve opener arms. At such time, the distal walls move radially inwardly to block the distal tip of the needle in a protective position.

As the needle continues to move in the proximal direction and the change in profile 144 on the needle engages the perimeter 282 on the proximal wall of the needle guard 132, the needle guard 132 is moved proximally with the needle 108. Alternatively the needle guard 132 can clamp onto the needle shaft 109 and be removed from the catheter hub 102 as a unit without utilizing a needle crimp. Note that in the protective position in which the needle guard 132 covers the needle tip 110, the valve 136 and the valve opener 134 remain inside the interior cavity of the catheter hub 102. Thus, the valve 136 and the valve opener 134 are located inside the catheter hub 102 in both the ready position of the needle and the protective position of the needle 108. Viewed from another perspective, the valve 136 and the valve opener 134 are located inside the catheter hub 102 in both the ready to use position of the catheter assembly 100, in which the needle tip projects out a distal opening 112 (FIG. 1) of the catheter tube 104, and a protective position of the catheter assembly 100, in which the needle 108 is removed from the catheter hub 102 and the needle tip 110 is covered by a needle guard 132.

With reference now to FIG. 7, the catheter hub 102 is shown with a male medical implement 220 positioned in the proximal opening thereof. The male medical implement or instrument 220 can be a male Luer, a syringe tip, an IV set connector, or other male tip having a Luer taper. For example, the male medical implement can be connected to an IV tubing, which is connected to an IV fluid source for fluid delivery through the male medical implement 220, the catheter hub 102, and the catheter tubing 104 to deliver fluid therapy to a patient.

When initially inserting the male medical implement 220, herein male tip, into the proximal opening of the catheter hub 102, the male tip initially contacts the two valve opener arms 152 on the valve opener 134 to advance a distally directed force on the two valve opener arms 152 to open the valve 136. The proximal end surfaces 151 of the valve opener arms 152 can provide a contact surface for the distal end of the male medical instrument 220, as previously discussed. The valve opener arms can also be designed to contact the inside wall of the catheter hub at a tangential point. In this way, the valve opener arms 152 are stable and can resist being deflected outwards. This arrangement can avoid relatively thin valve opener arms from wedging between the male medical instrument 220 and the inside wall of the catheter hub 102. The distally directed force moves the valve opener 134 in the distal direction until the geometries of the male tip 220 and the proximal opening 121 of the catheter hub 102 stop further distal advancement of the male tip. In an example, a female Luer taper of the catheter hub 102 and a male Luer taper of the male tip 220 register to form a Luer engagement and block distal advancement of the male tip further into the opening of the catheter hub. A seal can be provided by the Luer engagement to prevent fluid from leaking out the proximal opening 121 of the catheter hub 102.

As the valve opener 134 moves distally by the distal advancement of the male tip 220, the head 150 is urged distally and pushes against the proximally facing surface of the valve 136. In particular, the distal end of the valve opener 134 initially pushes against the proximally facing surface of the valve 136. As the valve 136 is fixed inside the catheter hub 102, the flaps of the valve 136 are urged distally by the valve opener 134, which is urged distally by the male tip 220. For example, the head 150 contacts and pushes the valve 136 in the distal direction thereby opening a flow path 226 through the valve opening 324 of the valve 136. Fluid from the male tip 220 can then flow through the catheter hub 102, through the valve 136, and through the lumen of the catheter tube 104. Alternatively, a suction can be applied by the male medical instrument, such as a syringe or vacuum blood collection tube, and blood aspirated from the patient. This is often done for testing samples before infusion therapy is commenced. Also, typically any remaining blood is first flushed from the inside of the catheter hub 102 before infusion therapy is commenced.

With further reference to FIGS. 11A to 15C, the shape of the head 150 or features on the head 150 of the various valve openers can facilitate deflection of the flaps on the valve 136 radially outwardly and in the distal direction, and can facilitate retracting the valve opener in the proximal direction to close or seal the valve. The heads 150 can be designed as a one-time use. That is, the heads of the various valve openers can be designed such that they stick to the valve or contact the valve in such a way that does not allow the flaps to uncoil even after removal of the male Luer tip and the no axial load is applied on the valve opener.

Thus, an aspect of the present disclosure is understood to include a catheter assembly comprising a valve comprising comprises plurality of slits defining a plurality of flaps that move in a distal direction to open a flow path through the valve, a valve opener configured to move the flaps of the valve, and a needle guard extending into the valve opener and having distal walls biased radially by the needle shaft or by the valve opener. The biased distal walls of the needle guard can engage a guard engagement section extending from inside the interior cavity of the catheter hub, can engage bumps or projections on the valve opener arms, or not engage any projection or bumps when the distal walls are biased outwardly by clip seats on the valve opener.

To change the male tip or to simply close the valve from the open position, the male tip can be removed in the proximal direction away from the catheter hub, which removes the axial load on the valve opener. The biasing or resilient nature of the valve, which can be made from an elastomer, allows the valve to recoil to its more relaxed state. Thus, the flaps on the valve will recoil by moving proximally, which pushes the valve opener in the proximal direction inside the interior cavity of the catheter hub. The valve opener therefore can return to its original position after removal of the male tip from the catheter hub. In some examples, an elastic gasket or a helical spring may be used in the interior distal chamber of the catheter hub, distal of the valve, to help push the flaps close upon removal of the male Luer tip.

Methods of making and of using the catheter assemblies and their components described elsewhere herein are within the scope of the present disclosure.

Although limited embodiments of catheter assemblies and their components have been specifically described and illustrated herein, many modifications and variations will be apparent to those skilled in the art. For example the needle guard may be of one piece or can be integrated from more than one piece, such as from multiple pieces that can be all metal or a combination of metal and polymer materials, such as plastic. Furthermore, it is understood and contemplated that features specifically discussed for one catheter assembly or for one component may be adopted for inclusion with another catheter assembly or another component, provided the functions are compatible. Accordingly, it is to be understood that the catheter assemblies and their components constructed according to principles of the disclosed devices, systems, and methods may be embodied other than as specifically described herein. The valves and valve openers described herein can also be used with a needle hub by locating them inside a female Luer taper of the needle hub. The valves and valve openers can also be used in the female connector of an infusion needle or a blood collection device or a central venous catheter or peripherally inserted central catheter (PICC). In other words, the valves and valve openers can be used in any medical device intended for infusion or bodily fluid collection with a female Luer housing or hub. The disclosure is also defined in the following claims.

What is claimed is:

1. A needle assembly comprising:
   a needle hub with a needle having a needle shaft and a needle tip extending from a distal end of the needle hub;

a catheter hub having an interior surface defining an interior cavity;

a catheter tube attached to the catheter hub and having the needle extending through the catheter tube with the needle tip extending out a distal opening in a ready-to-use position;

a valve comprising a plurality of slits and a plurality of flaps defining an opening, said valve seated in the interior cavity of the catheter hub;

a needle guard comprising at least one arm extending from a proximal wall, said proximal wall having a perimeter defining a proximal opening;

a valve opener positioned in the interior cavity of the catheter hub and proximal of the valve in a first position, the valve opener comprising a head located distally of the needle guard and two valve opener arms extending in a proximal direction of the head and located in between the needle guard and the interior surface of the catheter hub, each of said two valve opener arms comprising a clip seat having the needle guard biased there against and having a width measured orthogonally to the needle shaft, and wherein the width of each clip seat is larger than a diameter of the needle shaft and larger than a range of diameters of needle shafts in which the diameter of the needle shaft falls into; and wherein the head of the valve opener is axially displaceable against the valve to open the valve in a second position.

2. The needle assembly according to claim 1, wherein the needle guard, in a ready-to-use position and during needle withdrawal prior to activation of the needle guard, engages a guard engagement section formed on the interior surface of the catheter hub.

3. The needle assembly according to claim 2, wherein the guard engagement section has an inside diameter and wherein the inside diameter is generally constant across the range of diameters of needle shafts from G18 to G24.

4. The needle assembly according to claim 1, wherein the valve opener comprises a pair of guide tabs, wherein each guide tab of the pair of guide tabs is on an exterior of each respective valve opener arm.

5. The needle assembly according to claim 4, wherein each guide tab of the pair of guide tabs is located in a corresponding slot formed in the interior cavity of the catheter hub.

6. The needle assembly according to claim 4, wherein the guide tabs, the two valve opener arms, and the two clip seats are formed continuously.

7. The needle assembly according to claim 1, wherein the width of each clip seat is larger than the range of diameters of needle shafts from G18 to G24.

8. The needle assembly according to claim 1, where each of the two valve opener arms comprises a channel defining a drain.

9. The needle assembly according to claim 1, further comprising a bridge connecting the two valve opener arms.

10. The needle assembly according to claim 1, wherein the head of the valve opener comprises a frusto-conical shaped distal end.

11. A method of making a needle assembly comprising:
providing a needle hub with a needle having a needle shaft and a needle tip extending from a distal end of the needle hub;

providing a catheter hub having an interior surface defining an interior cavity;

attaching a catheter tube to the catheter hub and disposing the needle through the catheter tube with the needle tip extending out a distal opening in a ready-to-use position;

placing a valve comprising a plurality of slits and a plurality of flaps defining an opening in the interior cavity of the catheter hub;

placing a valve opener in the interior cavity of the catheter hub proximal of the valve; and placing a needle guard in contact with the valve opener, said needle guard comprising at least one arm extending from a proximal wall, said proximal wall having a perimeter defining a proximal opening;

wherein the valve opener comprises a head located distally of the needle guard and two valve opener arms extending in a proximal direction of the head and located in between the needle guard and the interior surface of the catheter hub, each of said two valve opener arms comprising a clip seat having the needle guard biased there against and having a width measured orthogonally to the needle shaft, and wherein the width of each clip seat is larger than a diameter of the needle shaft and larger than a range of diameters of needle shafts in which the diameter of the needle shaft falls into; and wherein the head of the valve opener is axially displaceable against the valve to open the valve in a second position.

12. The method of claim 11, wherein the needle shaft has a diameter of a G18 needle.

13. The method of claim 12, wherein the needle assembly is a first needle assembly and the method comprises making a second needle assembly identical to the first needle assembly and wherein the needle shaft of the second needle assembly has a diameter of a G20 needle, G22 needle, or G24 needle.

14. The method of claim 11, wherein the needle guard, in a ready-to-use position and during needle withdrawal prior to activation of the needle guard, engages a guard engagement section formed on the interior surface of the catheter hub.

15. The method of claim 14, wherein the guard engagement section has an inside diameter and wherein the inside diameter is generally constant across the range of diameters of needle shafts from G 18 to G24.

16. The method of claim 11, wherein the valve opener comprises a pair of guide tabs, wherein each guide tab of the pair of guide tabs is on an exterior of each respective valve opener arm.

17. The method of claim 16, wherein the guide tabs are located in corresponding slots formed in the interior cavity of the catheter hub.

18. The method of claim 11, where each of the two valve opener arms comprises a channel defining a drain located on each of the two valve opener arms.

19. The method of claim 11, further comprising a bridge connecting the two valve opener arms.

20. The method of claim 11, wherein the head of the valve opener comprises a frusto-conical shaped distal end.

* * * * *